United States Patent
Berg et al.

Patent Number: 6,159,970
Date of Patent: Dec. 12, 2000

[54] COMBINATION OF A MONOAMINE OXIDASE INHIBITOR AND A H5-HT$_{1B}$ ANTAGONIST OR PARTIAL AGONIST

[75] Inventors: Stefan Berg, Ekerö; Svante Ross, Södertälje; Seth-Olov Thorberg, Strängnäs, all of Sweden

[73] Assignee: Astrazeneca AB, Sodertalje, Sweden

[21] Appl. No.: 09/171,578

[22] PCT Filed: Sep. 9, 1998

[86] PCT No.: PCT/SE98/01602

§ 371 Date: Oct. 21, 1998

§ 102(e) Date: Oct. 21, 1998

[87] PCT Pub. No.: WO99/13878

PCT Pub. Date: Mar. 25, 1999

[30] Foreign Application Priority Data

Sep. 18, 1997 [SE] Sweden .................. 9703376

[51] Int. Cl.$^7$ ............... A61K 31/535; A61K 31/495; A61K 31/50; A61K 31/135

[52] U.S. Cl. .............. 514/235.8; 514/237.8; 514/253.11; 514/253.12; 514/254.11; 514/255.03; 514/654

[58] Field of Search ........... 514/235.8, 253.11, 514/253.12, 254.11, 255.03, 237.8, 654

[56] References Cited

FOREIGN PATENT DOCUMENTS

| | | |
|---|---|---|
| 0533267 | 3/1993 | European Pat. Off. |
| 0533268 | 3/1993 | European Pat. Off. |
| 9734883 | 9/1997 | WIPO |

*Primary Examiner*—William R. A. Jarvis
*Attorney, Agent, or Firm*—White & Case LLP

[57] ABSTRACT

The invention relates to a combination of a first component (a) which is a monoamine oxidase inhibitor and a second component (b) which is selective h5-HT$_{1B}$ antagonist or partial agonist having the formula I

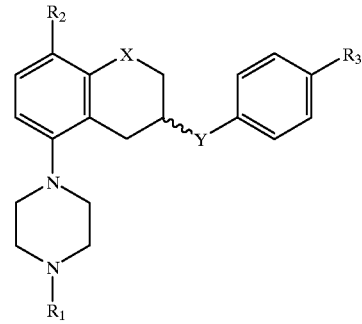

wherein X is CH$_2$, O;
Y is CONH, NHCO;
R$_1$ is H, C$_1$–C$_6$ alkyl, C$_3$–C$_6$ cycloalkyl;
R$_2$ is H, C$_1$–C$_6$ alkyl, C$_1$–C$_6$ alkoxy, halogen;
R$_3$ is

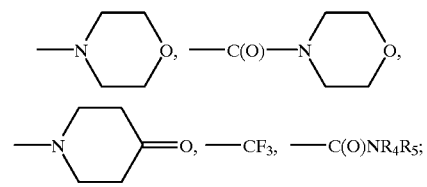

R$_4$ and R$_5$ independently are H or C$_1$–C$_4$ alkyl,
as racemate, R-enantiomer or S-enantiomer, and said components (a) and (b) being in the form of free bases, solvates or pharmaceutically acceptable salts thereof, the preparation thereof, pharmaceutical formulations containing said combination, use of and method of treatment of affective disorders such as depression, anxiety and OCD with said combination as well as a kit containing said combination.

23 Claims, 2 Drawing Sheets

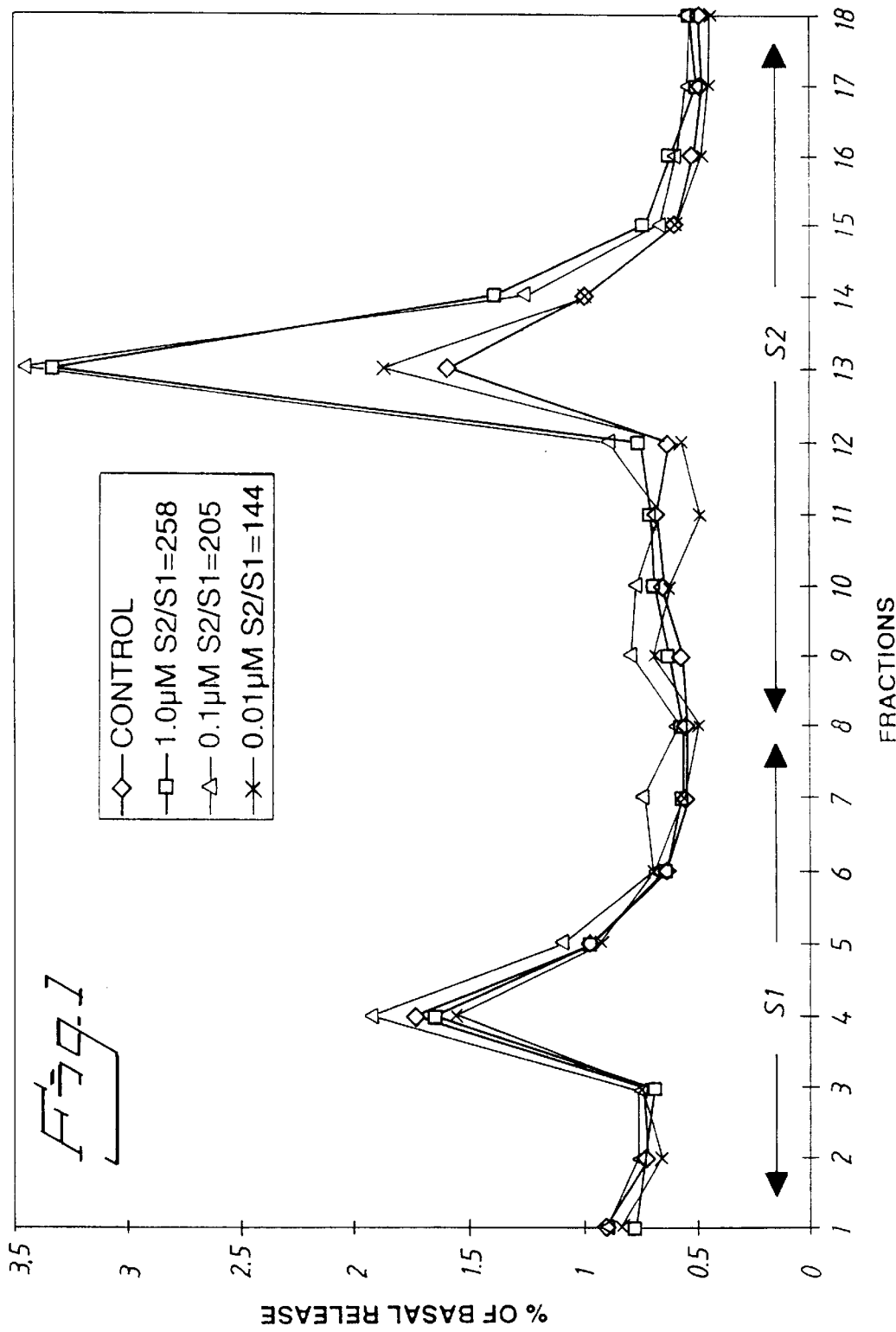

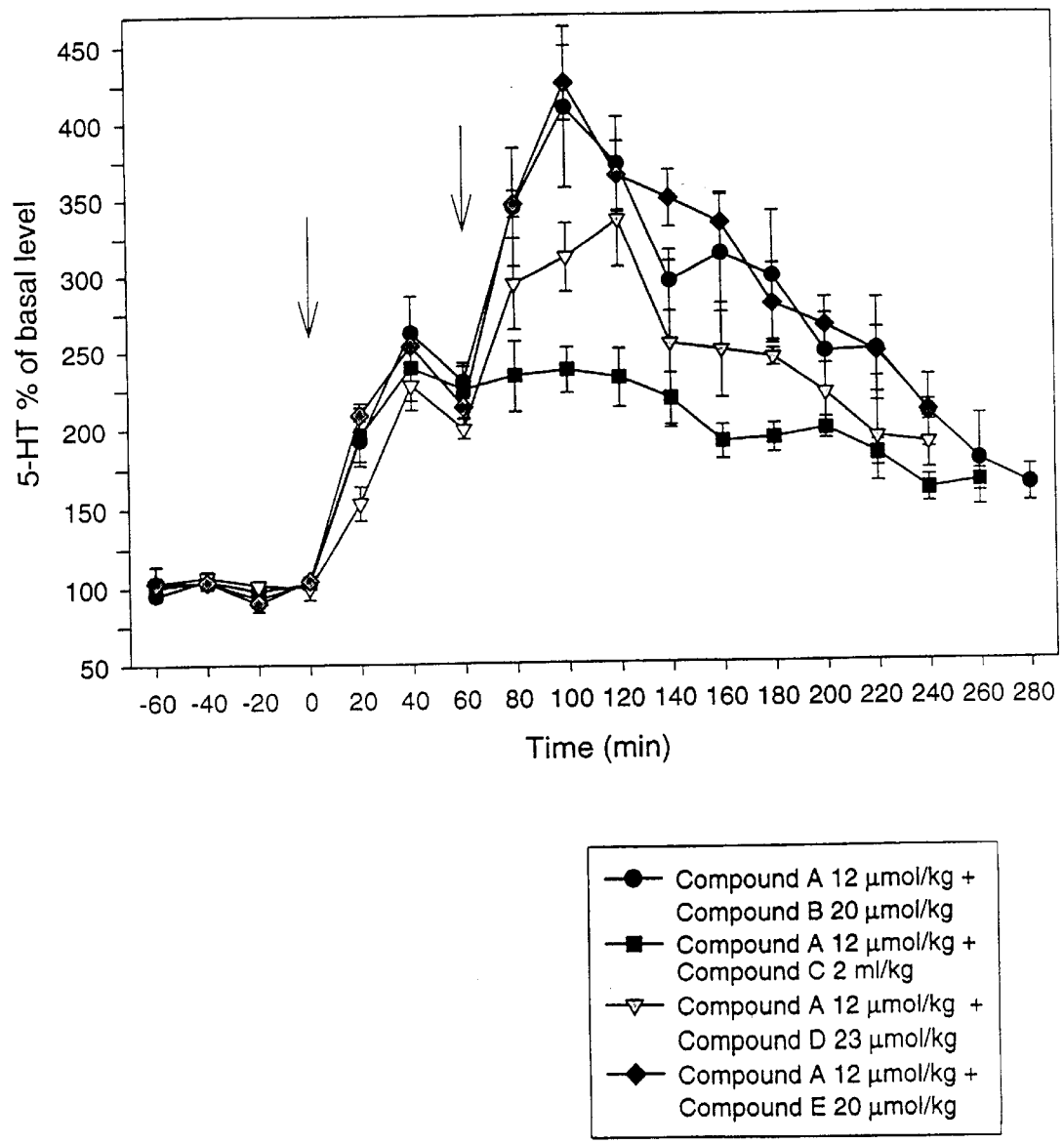

COMBINATION OF A MONOAMINE OXIDASE INHIBITOR AND A H5-HT$_{1B}$ ANTAGONIST OR PARTIAL AGONIST

This application is a 371 of PCT/SE98/01602, filed Sep. 9, 1998.

FIELD OF THE INVENTION

The present invention relates to a product which comprising a combination of a monoamine oxidase (MAO) inhibitor and a selective h5-HT$_{1B}$ receptor antagonist or partial agonist, more specifically a piperidyl- or piperazinyl-substituted 1,2,3,4-tetrahydronaphthalene or 3,4-dihydro-2H-1-benzopyran- derivative in the form of the free base solvates, or pharmaceutically acceptable salts thereof. The present invention also relates to a process for the preparation of the inventive combination, pharmaceutical formulation containing said combination and to the use of said combination by either concomitant administration or individual administration as an improvement of the treatment of affective disorders such as depression, anxiety, obsessive compulsive disorder (OCD), etc.

BACKGROUND OF THE INVENTION

Today, it is generally considered that antidepressants, including monoamine oxidase inhibitors (MAOI:s), take 2–4 weeks to reach their full clinical effect. In contrast, the side effects occur immediately. Thus, the slow onset of action of antidepressants leads to a vulnerable period for patients in which they experience the side effects, but not the therapeutic effects of drugs. There is often a heavy burden on the treating physician to persuade the patient to continue with the treatment during this period. Furthermore, in suicidal patients, as the onset of action is gradual, they may regain initiative without experiencing full reversal symptoms, leading to a window of risk for suicide and a frequent requirement for hospitalisation. An antidepressant with fast onset of action would not only be benificial due to the faster symptom reduction, but would also be more acceptable to patients and physicians and reduce the need for and duration of hospitalisation. The same long period to reach full clinical effect has been shown in the treatment of other affective disorders such as anxiety and OCD.

SUMMARY OF THE INVENTION

The present invention is directed, in part, to a combination of a MAO inhibitor and an antagonist or partial agonist of h5-HT$_{1B}$ receptor. Advantageously, treatment with the combination results in an enhanced release of 5HT.

The 5-HT transmission in the brain is negatively regulated by somatodrendritic 5-HT$_{1A}$ receptors (rate of cell firing) and the terminal h5-HT$_{1B}$ receptors (release of 5-HT). MAO inhibitors decrease the transmission of 5-HT by acting at both these sites. An antagonist of the terminal h5-HT$_{1B}$ receptors prevent the decrease in the 5-HT release at the nerve terminals resulting in an elevated concentration of synaptic 5-HT showing that antagonists of h5-HT$_{1B}$ receptors may have a clinical potential to improve the efficacy of MAO inhibitors and offer a new rational for rapid onset therapeutic actions.

BRIEF DESCRIPTION OF DRAWINGS

FIG. 1 shows the results of a functional h5-HT$_{1B}$ receptor assay.

FIG. 2 shows the effect of administering compound A (a monoamine oxidase inhibitor) in combination with compound B or C (a h5-HT$_{1B}$ antagonist or saline).

THE COMBINATION

Thus, by combining a first component (a) which is a monoamine oxidase inhibitor with a second component (b) which is a selective h5-HT$_{1B}$ antagonist or partial agonist having the formula I

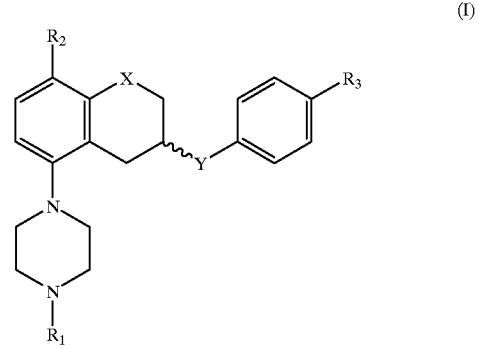

(I)

wherein X is CH$_2$, O;
Y is CONH, NHCO;
R$_1$ is H, C$_1$–C$_6$ alkyl, C$_3$–C$_6$ cycloalkyl;
R$_2$ is H, C$_1$–C$_6$ alkyl, C$_1$–C$_6$ alkoxy, halogen;
R$_3$ is

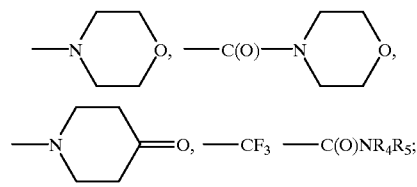

R$_4$ and R$_5$ independently are H or C$_1$–C$_4$ alkyl, as racemate, R-enantiomer or S-enantiomer, and said components (a) and (b) being in the in the form of free bases, solvates, preferably hydrates, or pharmaceutically acceptable salts thereof, a faster onset of action will occur and consequently, a more efficacious treatment of the patients.

In other preferred embodiments of the second component (b) are those compounds of formula I wherein X is CH$_2$, and of those compounds, compounds wherein Y is NHCO, and of those compounds, compounds wherein R$_3$ is morpholino. Compounds wherein R$_1$ is hydrogen, methyl or ethyl and wherein R$_2$ is hydrogen, methyl, ethyl, methoxy or bromo are preferred.

Preferred compounds having the formula I are:
(R)-N-[8-(Piperazin-1-yl)-1,2,3,4-tetrahydro-2-naphthyl]-4-morpholinobenzamide;
(R)-N-[8-(4-Ethylpiperazin-1-yl)-1,2,3,4-tetrahydro-2-naphthyl]-4-morpholinobenzamide;
(R)-N-[8-(4-Methylpiperazin-1-yl)-1,2,3,4-tetrahydro-2-naphthyl]-4-morpholinobenzamide;
(R)-N-[5-Methoxy-8-(4-methylpiperazin-1-yl)-1,2,3,4-tetrahydro-2-naphthyl]-4-morpholinobenzamide;
(R)-N-[5-Ethyl-8-(4-methylpiperazin-1-yl)-1,2,3,4-tetrahydro-2-naphthyl]-4-morpholinobenzamide;
(R)-N-[5-Ethyl-8-(4-methylpiperazin-1-yl)-1,2,3,4-tetrahydro-2-naphthyl]-(4-morpholinocarbonyl)benzamide;
(R)-N-[5-Methoxy-8-(4-methylpiperazin-1-yl)-1,2,3,4-tetrahydro-2-naphthyl]-4-morpholinocarbonylbenzamide;

(R)-N-[5-Bromo-8-(piperazin-1-yl)-1,2,3,4-tetrahydro-2-naphthyl]-4-morpholinobenzamide; N-[5-Bromo-8-(4-methylpiperazin-1-yl)-1,2,3,4-tetrahydro-2-naphthyl]-4-morpholinobenzamide;
(R)-N-[5-Bromo-8-(4-methylpiperazin-1-yl)-1,2,3,4-tetrahydro-2-naphthyl]-4-trifluoromethylbenzamide;
(R)-N-[5-Methyl-8-(4-methylpiperazin-1-yl)-1,2,3,4-tetrahydro-2-naphthyl]-4-morpholinobenzamide;
N-(4-Morpholinophenyl)-8-(4-methylpiperazinyl)-5-methoxy-1,2,3,4-tetrahydronaphthalene-2-carboxamide;
(R)-N-(4-Morpholinophenyl)-8-(4-methylpiperazinyl)-5-methoxy-1,2,3,4-tetrahydronaphthalene-2-carboxamide;
(S)-N-(4-Morpholinophenyl)-8-(4-methylpiperazinyl)-5-methoxy-1,2,3,4-tetrahydronaphthalene-2-carboxamide;
(R)- N-(Morpholinocarbonylphenyl)-8-(4-methylpiperazin-1-yl)-5-methoxy-1,2,3,4-tetrahydronaphthalene-2-carboxamide;
(S)-N-[5-(4-Methylpiperazin-1-yl)-3,4-dihydro-2H-1-benzopyran-3-yl]-4-morpholinobenzamide;
(S)-N-[5-(4-Methylpiperazin-1-yl)-3,4-dihydro-2H-1-benzopyran-3-yl]-4-(4-piperidon-1-yl)benzamide;
(S)-N-[8-Methyl-5-(4-methyl-piperazin-1-yl)-3,4-dihydro-2H-1-benzopyran-3-yl]-4-(dimethylaminocarbonyl)benzamide;
N-[4-(4-Morpholinyl)phenyl]-8-methoxy-5-(4-methyl-piperazin-1-yl)-3,4-dihydro-2H-1-benzopyran-3-carboxamide.

Particularly preferred compounds are (R)-N-[8-(4-Methylpiperazin-1-yl)-1,2,3,4-tetrahydro-2-naphthyl]-4-morpholinobenzamide, (R)-N-[5-Methoxy-8-(4-methylpiperazin-1-yl)-1,2,3,4-tetrahydro-2-naphthyl]-4-morpholinobenzamide and (R)-N-[5-Methyl-8-(4-methylpiperazin-1-yl)-1,2,3,4-tetrahydro-2-naphthyl]-4-morpholinobenzamide.

The compounds of formula I as (R)-enantiomers, (S)-enantiomers or racemates may exist in the form of a free base or a pharmaceutically acceptable salt or hydrate thereof.

In the present-context $C_1$–$C_6$ alkyl may be straight or branched. $C_1$–$C_6$ alkyl may be methyl, ethyl, n-propyl, i-propyl, n-butyl, i-butyl, s-butyl, t-butyl, n-pentyl, i-pentyl, t-pentyl, neo-pentyl, n-hexyl or i-hexyl. Preferred are $C_1$–$C_4$ alkyl and especially preferred are methyl and ethyl.

In the present context $C_1$–$C_4$ alkyl may be straight or branched. $C_1$–$C_4$ alkyl may be methyl, ethyl, n-propyl, i-propyl, n-butyl, i-butyl, s-butyl or t-butyl. Methyl and ethyl are preferred.

In the present context $C_3$–$C_6$ cycloalkyl may be cyclopropyl, cyclobutyl, cyclopentyl or cyclohexyl.

In the present context $C_1$–$C_6$ alkoxy may be straight or branched. $C_1$–$C_6$ alkoxy may be methoxy, ethoxy, n-propoxy, i-propoxy, n-butoxy, i-butoxy, s-butoxy, t-butoxy, n-pentyloxy, i-pentyloxy, t-pentyloxy, neo-pentyloxy, n-hexyloxy or i-hexyloxy. Preferred is $C_1$–$C_4$ alkoxy and especially preferred is methoxy.

In the present context halogen may be fluoro, chloro, bromo or iodo, wherein bromo is preferred.

Suitable known monoamine oxidase inhibitors (MAOI:s) to be used are moclobemide, phenelzine, tranylcypramine, brofaromide, preferably moclobemide or phenelzine but component (a) in the combination according to the invention is not limited only to these MAOI:s.

The combination according to the present invention may exist in one pharmaceutical formulation comprising both the active first component (a) and the active second component (b) or in two different pharmaceutical formulations, one for the active first component (a) and one for the active second component (b). The pharmaceutical formulation may be in the form of tablets or capsules, powders, mixtures, solutions or other suitable pharmaceutical formulation forms.

The combination of the present invention can be prepared by incorporating a MAO inhibitor into the same formulation as a selective h5-$HT_{1B}$ antagonist as defined above e.g. by mixing in a conventional way.

The present invention also includes a method of improving the onset of therapeutic action by concomitant administration of a combination of a first component (a) which is a MAO inhibitor and a second component (b) which is selective h5-$HT_{1B}$ antagonist as defined above.

A further embodiment of the present invention is a kit containing the combination of a first component (a) which is a MAO inhibitor and a second component (b) which is selective h5-$HT_{1B}$ antagonist as defined above. The kit may include an instruction for use.

Pharmaceutical formulations

According to the present invention the compounds in the combination will normally be administered orally, rectally or by injection, in the form of pharmaceutical formulations comprising the active ingredient either as a free base, solvates e.g. hydrates or a pharmaceutically acceptable non-toxic acid addition salt, e.g. the hydrochloride, hydrobromide, lactate, acetate, phosphate, sulfate, sulfamate, citrate, tartrate, oxalate and the like in a pharmaceutically acceptable dosage form. The dosage form may be a solid, semisolid or liquid formulation. Usually the active substances will constitute between 0.1 and 99% by weight of the formulation, more specifically between 0.5 and 20% by weight for formulations intended for injection and between 0.2 and 50% by weight for formulations suitable for oral administration.

The pharmaceutical formulation comprises the active ingredients, optionally in association with adjuvants, dilvents, excipients and/or inert carriers.

To produce pharmaceutical formulations of the combination of the invention in the form of dosage units for oral application, the selected compounds may be mixed with a solid excipient, e.g. lactose, saccharose, sorbitol, mannitol, starches such as potato starch, corn starch or amylopectin, cellulose derivatives, a binder such as gelatine or polyvinylpyrrolidone, disintegrants e.g. sodium starch glycolate, cross-linked PVP, cross-caramellose sodium and a lubricant such as magnesium stearate, calcium stearate, polyethylene glycol, waxes, paraffin, and the like, and then compressed into tablets. If coated tablets are required, the cores, prepared as described above, may be coated with a concentrated sugar solution which may contain e.g. gum arabic, gelatine, talcum, titanium dioxide, and the like. Alternatively, the tablets can be coated with a polymer known to the man skilled in the art, wherein the polymer is dissolved in a readily volatile organic solvent or mixture of organic solvents. Dyestuffs may be added to these coatings in order to readily distinguish between tablets containing different active substances or different amounts of the active compounds.

For the formulation of soft gelatine capsules, the active substances may be admixed with e.g. a vegetable oil or poly-ethylene glycol. Hard gelatine capsules may contain granules of the active substances using either the above mentioned excipients for tablets e.g. lactose, saccharose, sorbitol, mannitol, starches (e.g. potato starch, corn starch or amylopectin), cellulose derivatives or gelatine. Also liquids or semisolids of the drug can be filled into hard gelatine capsules.

Dosage units for rectal application can be solutions or suspensions or can be prepared in the form of suppositories comprising the active substances in a mixture with a neutral fatty base, or gelatine rectal capsules comprising the active substances in admixture with vegetable oil or paraffin oil. Liquid formulations for oral application may be in the form of syrups or suspensions, for example solutions containing from about 0.2% to about 20% by weight of the active substances herein described, the balance being sugar and mixture of ethanol, water, glycerol and propylene glycol. Optionally such liquid formulations may contain colouring agents, flavouring agents, saccharine and carboxymethylcellulose as a thickening agent or other excipients known to a person skilled in the art.

Solutions for parenteral applications by injection can be prepared in an aqueous solution of a water-soluble pharmaceutically acceptable salt of the active substances, preferably in a concentration of from about 0.5% to about 10% by weight. These solutions may also contain stabilizing agents and/or buffering agents and may conveniently be provided in various dosage unit ampoules.

Suitable daily doses of the active compounds in the combination of the invention in therapeutic treatment of humans are about 0.01–100 mg/kg bodyweight on peroral administration and 0.001–100 mg/kg bodyweight on parenteral administration. The daily doses of the active h5-HT$_{1B}$ antagonist may very well differ from the daily doses of the MAO inhibitor but the doses can also be the same for both of the active substances.

Medical and Pharmaceutical Use

In a further aspect the present invention provides the use of the combination of a first component (a) which is a MAO inhibitor with a second component (b) which is a selective h5-HT$_{1B}$ antagonist or partial agonist, preferably an antagonist, having the formula I as defined herein, and the use in the treatment of 5-hydroxytryptamine mediated disorders, such as affective disorders. Examples of affective disorders are disorders in the CNS such as mood disorders (depression, major depressive episodes, dysthymia, seasonal affective disorder, depressive phases of bipolar disorder), anxiety disorders (obsessive compulsive disorder, panic disorder with/without agoraphobia, social phobia, specific phobia, generalized anxiety disorder, posttraumatic stress disorder), personality disorders (disorders of impulse control, trichotellomania). Other disorders in CNS such as obesity, anorexia, bulimia, premenstrual syndrome, sexual disturbances, alcoholism, tobacco abuse, autism, attention deficit, hyperactivity disorder, migraine, memory disorders (age associated memory impairment, presenile and senile dementia), pathological aggression, schizophrenia, endocrine disorders (e g hyperprolactinaemia), stroke, dyskinesia, Parkinson's disease, thermoregulation, pain, hypertension may be treated with the combination described herein, too. Examples of hydroxytryptamine mediated disorders are urinary incontinence, vasospasm and growth control of tumors (e g lung carcinoma) and it may be possible to treat those with the combination described herein as well.

Method of Preparation of Intermediates.

1. In the case where Y is NHCO and X is CH$_2$ or O.

(i) Benzylation of the compound of the formula II, either as a racemate or as an enantiomer,

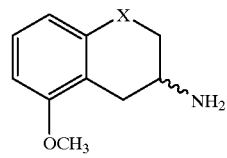

(II)

to obtain a compound of formula III may be carried out by reaction with a suitable benzylation agent e.g. a benzyl halide such as benzyl bromide or benzyl chloride or an activated alcohol e.g. benzyl mesylate or benzyl tosylate. The reaction may be carried out using a salt or the base of compound II in a suitable solvent e.g. N,N-dimethylformamide, acetone or acetonitrile with a suitable base e.g. NaOH, NaHCO$_3$, K$_2$CO$_3$ or a trialkylamine such as triethylamine at a temperature within the range of +20° C. to +150° C. The presence of a suitable catalyst e.g. potassium iodide or sodium iodide, may increase the speed of the reaction. The nitrogen in compound II may also be protected by reductive alkylation with an arylaldehyde in the presence of a reductive agent such as sodium cyanoborohydride, sodium borohydride or catalytically with H$_2$ and a suitable catalyst containing palladium, platinum, rhodium or nickel in a suitable solvent e.g. tetrahydrofuran, dioxane, methanol or ethanol. A proton donor such as p-toluenesulfonic acid can be used to catalyze the formation of the imine/enamine, and adjustment of pH to slightly acidic by an appropriate acid such as acetic acid may speed up the reaction, resulting in compound III.

(ii) Demethylation of the compound of formula III

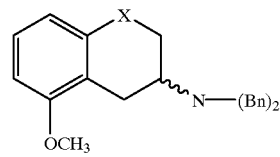

(III)

to obtain a compound of formula IV may be carried out by treating the compound with an acidic reagent such as aqueous HBr, HI, HBr/CH$_3$COOH, BBr$_3$, AlCl$_3$, pyridine-HCl or with a basic nucleophilic reagent such as CH$_3$C$_6$H$_4$S$^-$ or C$_2$H$_5$S$^-$ in a suitable solvent. Suitable solvents may be methylene chloride or chloroform and the reaction may occur between −78° C. and +60° C.

(iii) Conversion of the compound of formula IV to a compound of formula V

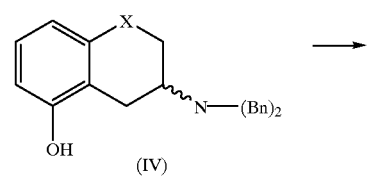

(IV)

-continued (V)

may be carried out by the reaction with a compound of formula VI (VI)

where L stands for a leaving group, e.g. a halogen such as chlorine, bromine or iodine or an alkane- or arenesulfonyloxy group such as a p-toluenesulfonyloxy group and Ra and Rb are hydrogen or a lower alkyl group e.g. methyl. The process may be carried out with a salt of the compound of formula IV obtained by reaction with a base such as $K_2CO_3$, $Na_2CO_3$, KOH, NaOH, BuLi or NaH. The reaction may be conducted in a suitable solvent e.g. an aprotic solvent such as dioxane, N,N-dimethylformamide, tetrahydrofuran, toluene, benzene or petroleum ether and the reaction may occur between +20° C. and +150° C.

(iv) Rearrangement of a compound of formula V to a compound of formula VII (V)

(VII)

may be carried out in a suitable solvent e.g. aprotic solvent such as N,N dimethylformamide, dioxane, 1,1,3,3-tetramethylurea, tetrahydrofuran or hexamethylphosphoric triamide with a suitable base e.g. $K_2CO_3$, KOH, potassium tert-butoxide or NaH at a temperature within the range of +20° C. to +150° C. The presence of a cosolvent such as 1,3-dimethyl-3,4,5,6-tetrahydro-2(1H)-pyrimidone or hexamethylphosphoric triamide in appropriate concentration in the solvent may increase the speed of the reaction.

(v) Hydrolysis of a compound of formula VII to a compound VIII may be carried out under acidic conditions using acids such as $H_2SO_4$, HCl or HBr in a suitable solvent e.g. $H_2O$, ethanol, methanol or mixtures thereof and the reaction may occur between +20° C. and +100° C. or under basic conditions using bases such as NaOH or KOH in a suitable solvent e.g. $H_2O$, ethanol, methanol or mixtures thereof and the reaction may occur between +20° C. and +100° C.

(vi) Conversion of compound of formula VIII to a compound of formula IX (VIII)

(IX)

may be carried out by a) reaction with a compound of formula X (X)

where $R_1$ is $C_1$–$C_6$ alkyl or $C_3$–$C_6$ cycloalkyl. The process may be carried out in a suitable is solvent e.g. an aprotic/anhydrous solvent such as tetrahydrofuran or N,N-dimethylformamide in the presence of coupling reagent such as N,N'-carbonyldiimidazole and the reaction may occur between +20° C. and +130° C. The reaction is followed by the reduction of the imide with a suitable reducing agent e.g. $LiAlH_4$ in a suitable solvent e.g. diethyl ether or tetrahydrofuran at a temperature between +20° C. and reflux, or b) by reaction with a compound of formula XI

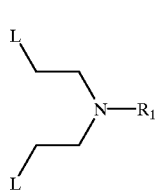

(XI)

where L stands for a leaving group, e.g. a halogen such as chlorine or bromine or an alkane- or arenesulfonyloxy group such as p-toluenesulfonyloxy group and $R_1$ is H, $C_1$–$C_6$-alkyl or $C_3$–$C_6$ cycloalkyl. The process may be carried out in a suitable solvent such as ethanol, buthanol, N,N-dimethylformamide, acetonitrile or a mixture of water and acetonitrile with a suitable base e.g. $K_2CO_3$, $NaHCO_3$ or KOH and the reaction may occur between +20° C. and +150° C.

Conversion of a compound of formula IX, wherein $R_1$ is hydrogen, to an alkylated compound of formula IX, where $R_1$ is $C_1$–$C_6$ alkyl, may be carried out by using a suitable alkylation reagent such as $R_1$—L, where L is a suitable leaving group e.g. a halogen such as chlorine, bromine or iodine or an alkane- or arenesulfonyloxy group such as a p-toluenesulfonyloxy group and $R_1$ is $C_1$–$C_6$ alkyl. The reaction may be carried out in a suitable solvent such as N,N-dimethylformamide, acetone, acetonitrile or tetrahydrofuran with a suitable base such as $K_2CO_3$, $NaHCO_3$, NaOH or a trialkylamine such as triethylamine. The reaction may be conducted at a temperature between +20° C. and +120 ° C., or conversion of a compound of formula IX, where $R_1$ is hydrogen, to an alkylated compound of formula IX, where $R_1$ is $C_1$–$C_6$ alkyl or $C_3$–$C_6$ cycloalkyl, may be carried out by reductive alkylation with a compound $R_1$—CHO, where $R_1$ is hydrogen or $C_1$–$C_5$ alkyl, or with a $C_3$–$C_6$ cyclic ketone, in the presence of a reductive agent such as sodium cyanoborohydride, sodium borohydride or catalytically with $H_2$ and a suitable catalyst containing palladium, platinium, rhodium or nickel in a suitable solvent e.g. tetrahydrofuran, dioxane, methanol or ethanol. A proton donor such as p-toluenesulfonic acid can be used to catalyze the formation of the imine/enamine and adjustment of pH to slightly acidic by an appropriate acid such as acetic acid may speed up the reaction.

(vii) Halogenation of the compound of formula IX, where $R_1$ is hydrogen, $C_1$–$C_6$-alkyl or $C_3$–$C_6$-cycloalkyl,

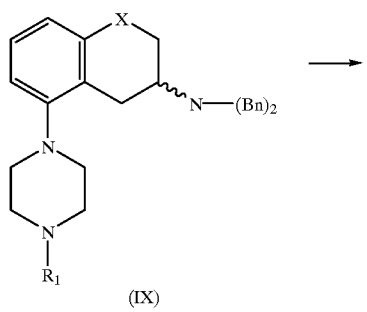

(IX)

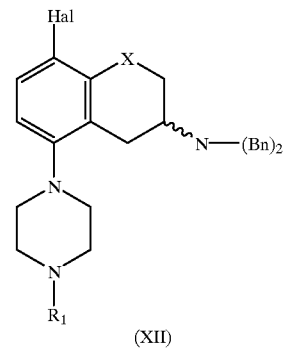

(XII)

to obtain a compound of formula XII may be performed by aromatic electrophilic substitution using a suitable halogenation agent such as $Br_2$, $Cl_2$, $I_2$, ICl, or $SO_2Cl_2$. The reaction may be carried out using the salt or the base of the compound IX in an appropriate solvent e.g. acetic acid, HCl/ethanol or water with or without a suitable base e.g. alkali metal acetate such as sodium acetate and at a reaction temperature between −20° C. and room temperature.

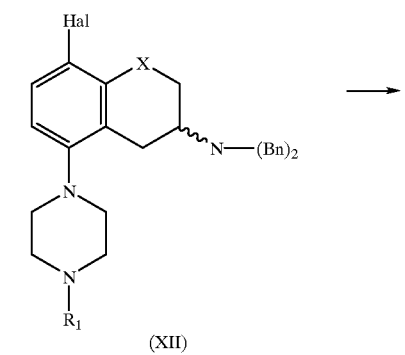

(XII)

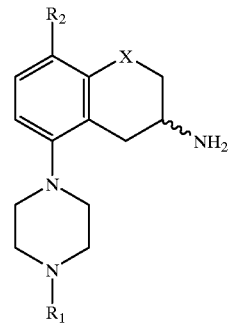

(XIII)

(viii) Conversion of the compound of formula XII to a compound of formula XIII, where $R_1$ is hydrogen, $C_1$–$C_6$ alkyl or $C_3$–$C_6$ cycloalkyl and $R_2$ is $C_1$–$C_6$ alkyl, may be carried out by a metal-halogen exchange, in a appropriate anhydrous solvent such as tetrahydrofuran or diethyl ether using a suitable alkyl-lithium or metal e.g. buthyllithium, lithium or magnesium turnings, followed by treatment with appropriate alkyl halide such as methyl iodide, ethyl bromide or propyl iodide and the reaction may be performed at a reaction temperature within the range of −78° C. to room temperature, followed by cleavage of the benzyl groups by hydrogenation over a suitable catalyst containing palladium, rhodium, platina or nickel, in a suitable solvent e.g. acetic acid or ethanol and at a reaction temperature between +20° C. and +120° C., or treatment with other electrophiles such as acetaldehyde or methyl chloroformate and a thereafter following suitable work-up. The reaction may be performed at a reaction temperature within the range of −78° C. to room temperature.

In the case where acetaldehyde is used as electrophile, the above reaction is followed by reduction of the benzyl alcohol and cleavage of the benzyl groups by hydrogenation over a suitable catalyst containing palladium, rhodium, platina or nickel, in a suitable solvent e.g. acetic acid or ethanol and the reaction may occur between +20° C. and +120° C.

In the case where methyl chloroformate is used as electrophile, the above reaction is followed by reduction of the methyl ester in a suitable solvent such as diethyl ether or tetrahydrofuran with an appropriate reductive agent such as lithium aluminum hydride and the reaction may occur between +20° C. and reflux, followed by cleavage of the benzyl groups and reduction of the benzyl alcohol by hydrogenation over a suitable catalyst containing palladium, rhodium, platina or nickel, in a suitable solvent e.g. acetic acid or ethanol and the reaction may occur between +20° C. and +120° C.

When $R_1$ is hydrogen, the piperazine nitrogen is protected with a suitable protecting group to before the lithiation step such as a benzyl group or another protecting group known by a person skilled in the art and then removed by methods known by a person skilled in the art, resulting in the compound of formula XIII.

(ix) Conversion of a compound of formula XIII, where $R_1$ is hydrogen, to a compound of formula XIV,

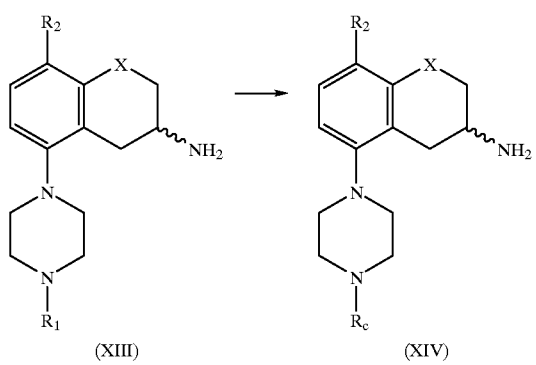

where $R_c$ is a suitable protecting group, may be carried out by the protection of the piperazine ring in a suitable solvent e.g. methylene chloride or chloroform with a appropriate protecting reagent e.g. di-tert-butyl dicarbonate with a suitable base e.g. triethylamine or $K_2CO_3$ and at a temperature between −20° C. and +60° C.

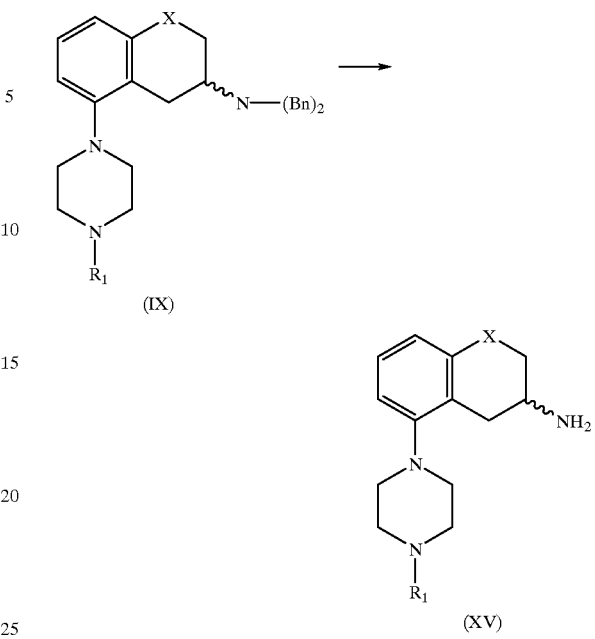

(x) Conversion of the compound of formula IX, where $R_1$ is hydrogen, $C_1$–$C_6$ alkyl or $C_3$–$C_6$ cycloalkyl, to a compound of formula XV, where $R_1$ is hydrogen, $C_1$–$C_6$ alkyl or $C_3$–$C_6$ cycloalkyl may be carried out by cleavage of the benzyl groups by hydrogenation over a suitable catalyst containing palladium, rhodium, platina or nickel, in a suitable solvent e.g. acetic acid or ethanol and the reaction may occur between +20° C. and +120° C.

(xi) Conversion of a compound of formula IX where $R_1$ is hydrogen, to a compound of formula XVI

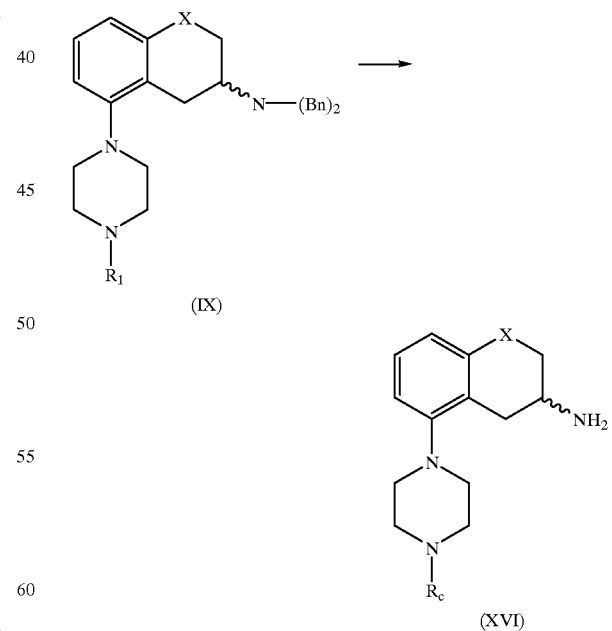

where $R_c$ stands for a suitable protecting group, may be carried out by a) hydrogenation using a catalyst containing palladium, platinum, rhodium or nickel in a suitable solvent e.g.

acetic acid or ethanol at a reaction temperature between +20° C. and +120° C., or b) debenzylation in a suitable solvent such as methanol in the presence of ammonium formate and Pd/C at a reaction temperature between +20° C. and reflux.

Said reaction is followed by the protection of the piperazine ring in a suitable solvent e.g. methylene chloride or chloroform with an appropriate protecting reagent e.g. di-tert-butyl dicarbonate with a suitable base e.g. triethylamine or $K_2CO_3$ and at a temperature between –20° C and +60° C.

(xii) Halogenation of the compound of formula XV, where $R_1$ is hydrogen, $C_1$–$C_6$-alkyl or $C_3$–$C_6$-cycloalkyl,

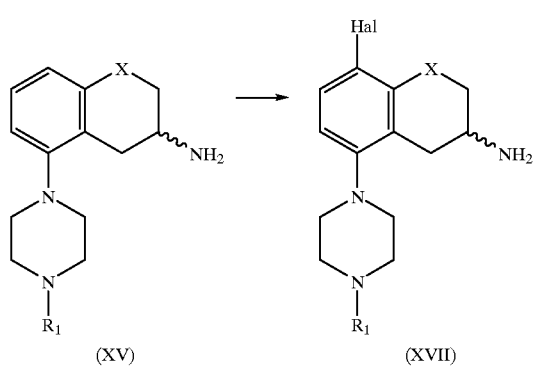

to obtain a compound of formula XVII may be performed by aromatic electrophilic substitution using a suitable halogenation agent such as $Br_2$, $Cl_2$, $I_2$, ICl, or $SO_2Cl_2$. The reaction may be carried out using the salt or the base of the compound XV in a appropriate solvent e.g. acetic acid, HCl/ethanol or water with or without a suitable base e.g. alkali metal acetate such as sodium acetate and at a reaction temperature between –20° C. and room temperature.

(xiii) Conversion of a compound of formula XVII, where $R_1$ is hydrogen, to a compound of formula XVIII,

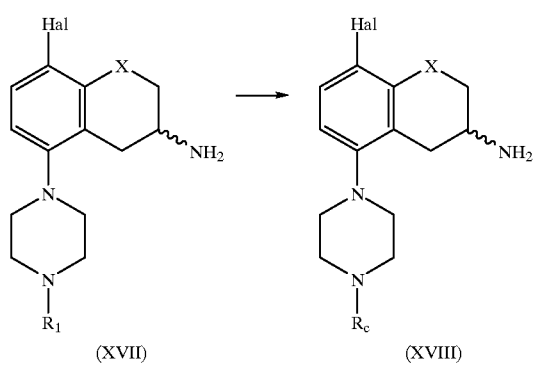

where $R_c$ is a suitable protecting group, may be carried out by the protection of the piperazine ring in a suitable solvent e.g. methylene chloride or chloroform with an appropriate protecting reagent e.g. di-tert-butyl dicarbonate with a suitable base e.g. triethylamine or $K_2CO_3$ and at a temperature between –20° C. and +60° C.

(xiv) Halogenation of the compound of formula XIX, where $R_2$ is $C_1$–$C_6$ alkoxy (when X is 0 described in: Thorberg, S-O et al. *Acta Pharm. Suec.* 1987 24, 169–182; when X is $CH_2$ commercially available) either as racemate or as an enantiomer

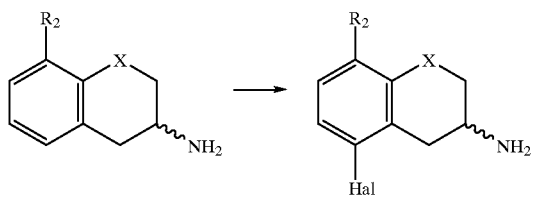

to obtain a compound of formula XX may be performed by aromatic electrophilic substitution using a suitable halogenation agent such as $Br_2$, $Cl_2$, $I_2$, ICl, or $SO_2Cl_2$. The reaction may be carried out using the salt or the base of the compound XIX in an appropriate solvent e.g. acetic acid, HCl/ethanol or water with or without a suitable base e.g. alkali metal acetate such as sodium acetate and at a reaction temperature between –20 ° C. and room temperature.

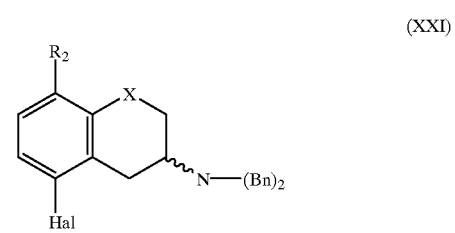

(xv) Benzylation of the compound of the formula XX, either as a racemate or as an enantiomer, to obtain a compound of the formula XXI by reaction with a suitable benzylation agent e.g. benzyl halide such as benzyl bromide or benzyl chloride or an activated alcohol e.g. benzylmesylate or -tosylate. The reaction may be carried out using the salt or the base of compound of formula XX in a suitable solvent e.g. N,N-dimethylformamide, acetone or acetonitrile with a suitable base such as triethylamine, NaOH, $NaHCO_3$ or $K_2CO_3$ at a temperature within the range of +20° C. to +150° C. The presence of a suitable catalyst e.g. alkali metal halide such as potassium iodide or sodium iodide may increase the speed of the reaction.

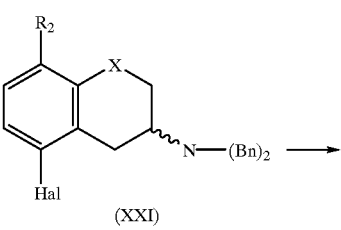

-continued

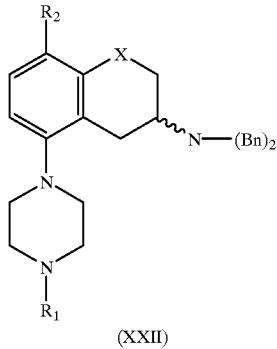

(XXII)

(xvi) Conversion of the compound of formula XXI to a compound of formula XXII, where $R_1$ is hydrogen, $C_1$–$C_6$ alkyl or $C_3$–$C_6$ cycloalkyl and $R_2$ is $C_1$–$C_6$ alkoxy, may be carried out by the reaction with a compound of formula XXIII, where $R_1$ is hydrogen, $C_1$–$C_6$ alkyl or $C_3$–$C_6$ cycloalkyl.

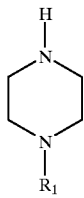

(XXIII)

The process may be carried out in a suitable solvent e.g. an aprotic solvent such as benzene, toluene, dioxane, tetrahydrofuran or N,N-dimethylformamide with a suitable base such as sodium tert-butoxide or lithium bis(trimethylsilyl)amide in the presence of a suitable palladium catalyst such as $PdZ_2$, $L'_2Pd(O)$ or $L'_2PdZ_2$ where Z stands for a halogen such as chlorine or bromine and L' stands for a suitable ligand such as triphenylphosphine, tri-o-tolylphosphine, trifurylphosphine, triphenylarsine or dibenzylideneacetone and with or without an addition of a ligand L'' such as triphenylphosphine, tri-o-tolylphosphine, trifurylphosphine, 2,2'-bis(diphenylphosphino)-1,1'-binaphthalene (either as a racemate or as an enantiomer) or triphenylarsine and the reaction may occur at a temperature between +20° C. and +150° C.

(xvii) Conversion of the compound of formula XXII to a compound of formula XXIV

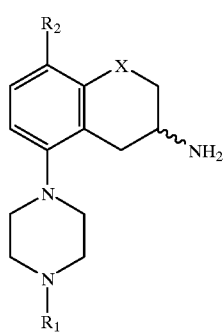

(XXIV)

where $R_1$ is hydrogen, $C_1$–$C_6$ alkyl or $C_3$–$C_6$ cycloalkyl and $R_2$ is $C_1$–$C_6$ alkoxy may be carried out by hydrogenation using a catalyst containing palladium, platinum, rhodium or nickel in a suitable solvent e.g. acetic acid or ethanol at a reaction temperature between +20 ° C. and +120° C.

(xviii) Conversion of compound of formula XXIV, where $R_1$ is hydrogen, to a compound of formula XXV,

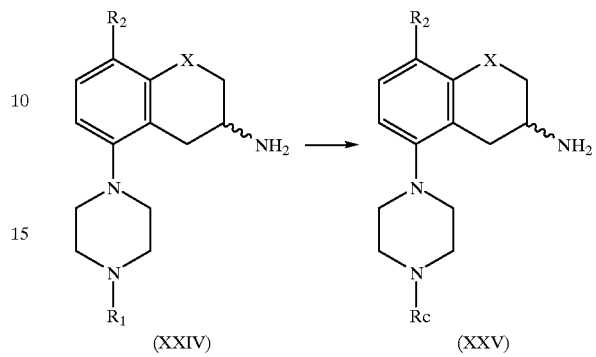

(XXIV)        (XXV)

where $R_c$ is a suitable protecting group, may be carried out by the protection of the piperazine ring in a suitable solvent e.g. methylene chloride or chloroform with a appropriate protecting reagent e.g. di-tert-butyl dicarbonate with a suitable base e.g. triethylamine or $K_2CO_3$ and at a temperature between −20° C. and +60° C.

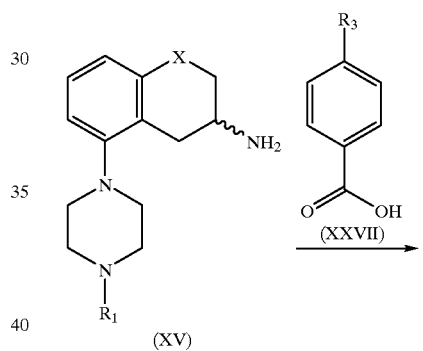

(XV)

(XXVII)

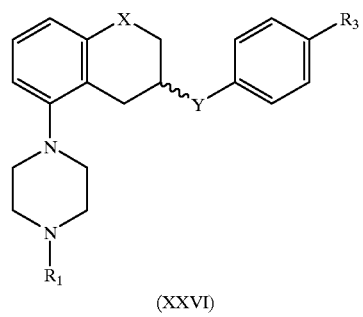

(XXVI)

(xix) Conversion of a compound of formula XV, where $R_1$ is $C_1$–$C_6$ alkyl or $C_3$–$C_6$ cykloalkyl, to a compound of formula XXVI, where Y is NHCO and $R_3$ is as defined in general formula I above, may be carried out by acylation with an appropriate benzoic acid of formula XXVII activated as an acid chloride in a suitable solvent such as methylene chloride or chloroform with a suitable base e.g. trialkylamine such as triethylamine or by using a benzoic acid of formula XXVII with an activating reagent e.g. N,N'-carbonyldiimidazole, N,N'-dicyclohexylcarbodiimide or diphenylphosphinic chloride with a suitable base such as N-methylmorpholine in a suitable solvent such as N,N-dimethylformamide or tetrahydrofuran and the reaction may be conducted at a temperature between +20° C. and +150° C.

2. It the case where Y is CONH and X is CH$_2$ or O.

(i) Nitration of a compound of formula XXVIII, where R$_2$ is C$_1$–C$_6$ alkoxy, either as a racemate or as an enantiomer, to obtain a compound of formula XXIX,

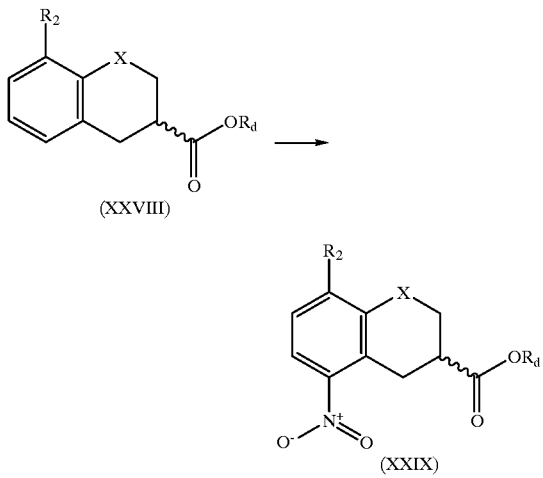

where R$_d$ is C$_1$–C$_6$ alkyl, may be carried out by aromatic electrophilic substitution using a suitable nitration reagent such as nitric acid or nitric acid and sulphuric acid in a suitable solvent e.g. acetic acid, acetic anhydride or water at a reaction temperature between −20° C. and room temperature.

(ii) Hydrolysis of a compound of formula XXIX may be carried out under acidic conditions using acids such as H$_2$SO$_4$, HCl, HBr, in a suitable solvent such as H$_2$O, ethanol, methanol, acetic acid or mixtures thereof and the reaction may occur at a temperature between +20° C. and reflux or under basic conditions using bases such as NaOH or KOH in a suitable solvent such as H$_2$O, ethanol, methanol or mixtures thereof and the reaction may occur at a temperature between +20° C. and reflux, resulting in a compound of formula XXX.

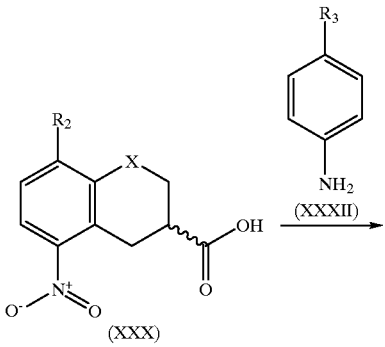

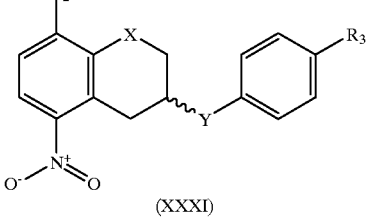

(iii) Conversion of a compound of formula XXX, where R$_2$ is C$_1$–C$_6$ alkoxy, to a compound of formula XXXI, where Y is CONH and R$_2$ is C$_1$–C$_6$ alkoxy may be carried out by activation of the acid function of a compound of formula XXX as an acid halide such as an acid chloride with a suitable base such as a trialkylamine e.g. triethylamine or by using an activating reagent such as N,N'-carbonyldiimidazole, N,N-dicyclohexylcarbodiimide or diphenylphosphinic chloride with a suitable base such as N-methylmorpholine in a suitable solvent e.g. methylene chloride, chloroform, toluene, N,N-dimethylformamide, dioxane or tetrahydrofuran followed by the addition of an appropriate aniline XXXII, where R$_3$ is as defined in formula I above. The reaction may occur between 0° C. and +120° C.

(iv) Conversion of the compound of formula XXXI to a compound of formula XXXIII, where Y is CONH and R$_3$ is as defined in general formula I may be carried out by

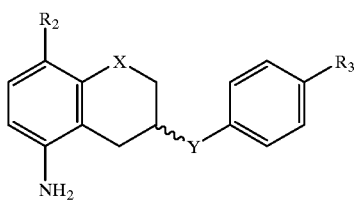

hydrogenation using a catalyst containing palladium, platina or nickel in a suitable solvent such as ethanol, methanol or acetic acid at a reaction temperature between +20° C. and +120° C.; or reduction with sodium dithionite in a suitable solvent.

3. Conversion of a compound of formula XXXIV to a compound of formula XXXV

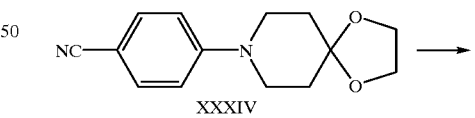

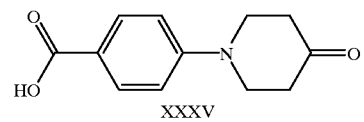

may be carried out by
a) hydrolysis of the nitrile in compound of formula XXXIV in a suitable solvent such as aqueous methanol or aqueous ethanol in the presence of a suitable base such as NaOH or KOH at a reaction temperature between room temperature and reflux, followed by
b) hydrolysis of the above formed amide and the ketal under acidic conditions in a suitable solvent such as aqueous methanol, aqueous ethanol or water in the presence of a suitable acid such as HCl or HBr at a reaction temperature between room temperature and reflux.

Methods of Preparation of End Products

Another object of the invention is a process A(i), A(ii), B or C for the preparation of the compound of general formula I by A(i)

acylation, in the case where $R_1$ is $C_1$–$C_6$ alkyl or $C_3$–$C_6$ cycloalkyl, Y is NHCO and X, $R_2$ and $R_3$ are as defined in general formula I above, of a compound of formula A,

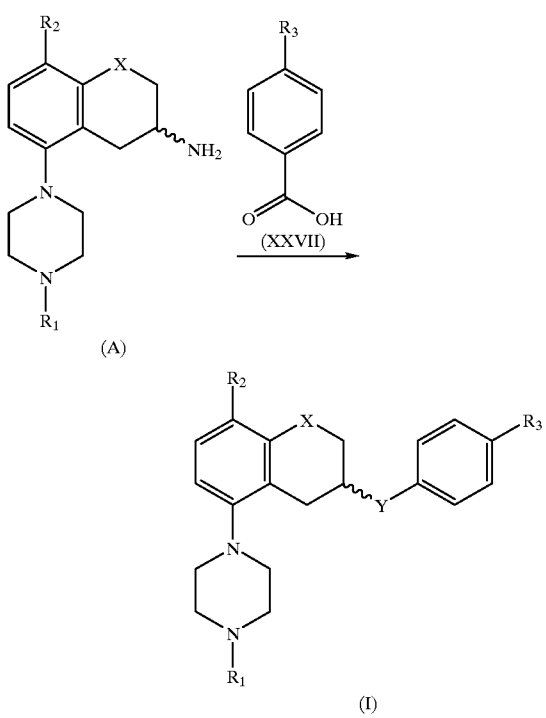

(A)

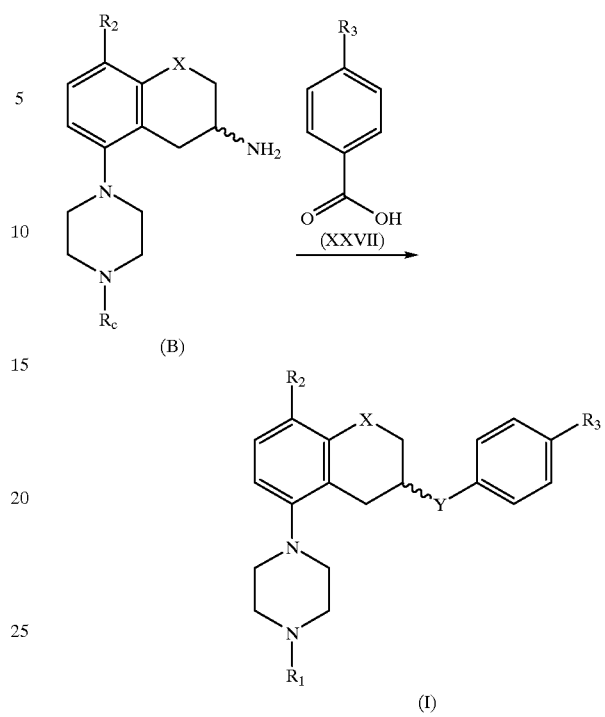

(B)

with an activated benzoic acid of formula XXVII or by using a benzoic acid of formula XXVII with an activating reagent.

Thus, the acylation according to the process A(i) may be carried out with an appropriate benzoic acid of formula XXVII, where $R_3$ is as defined in formula I above, activated as an acid chloride in a suitable solvent such as methylene chloride or chloroform with a suitable base e.g. trialkylamine such as triethylamine at a temperature between –20° C. and reflux temperature or by using an benzoic acid of formula XXVII, where $R_3$ is as defined in formula I above, with an activating reagent e.g. N,N'-carbonyldiimidazole, N,N'-dicyclohexylcarbodiimide or diphenylphosphinic chloride with a suitable base such as N-methylmorpholine in a suitable solvent such as N,N-dimethylformamide or tetrahydrofuran and the reaction may be conducted at a temperature between +20° C. and +150° C.

A(ii) acylation, in the case where $R_1$ is hydrogen, Y is NHCO, $R_c$ is a protecting group and X, $R_2$ and $R_3$ are as defined in general formula I above, of a compound of formula B Thus, the acylation according to the process A(ii) may be carried out with an appropriate benzoic acid of formula XXVII, where $R_3$ is as defined in formula I above, activated as an acid chloride in a suitable solvent such as methylene chloride or chloroform with a suitable base e.g. trialkylamine such as triethylamine at a temperature between –20° C. and reflux temperature or by using an benzoic acid of formula XXVII, where $R_3$ is as defined in formula I above, with an activating reagent e.g. N,N'-carbonyldiimidazole, N,N'-dicyclohexylcarbodiimide or diphenylphosphinic chloride with a suitable base such as N-methylmorpholine in a suitable solvent such as N,N-dimethylformamide or tetrahydrofuran and the reaction may be conducted at a temperature between +20° C. and +150° C. followed is by removal of the protecting group $R_c$ by hydrolysis in a suitable solvent such as methylene chloride or chloroform with a suitable acid such as trifluoroacetic acid at a temperature between +20° C. and +60° C.

B reacting, in the case where Y is CONH, X, $R_1$, $R_2$ and $R_3$ are as defined in general formula I above,

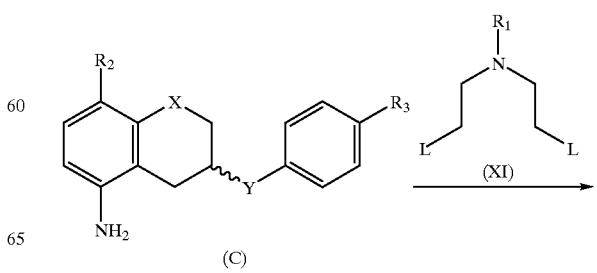

(C)

-continued (I)

with a compound of formula XI wherein L is a leaving group. Thus, the reaction according to the process B may be carried out with a compound of formula XI wherein $R_1$ is as defined in general formula I above and L is a leaving group, e.g. a halogen such as chlorine or bromine or an alkane- or arenesulfonyloxy group such as p-toluene-sulfonyloxy group. The process may be carried out in a suitable solvent such as ethanol, butanol, N,N-dimethylformamide, acetonitrile or a mixture of water and acetonitrile with or without a suitable base e.g. $K_2CO_3$, $NaHCO_3$ or KOH and the reaction may occur between +20° C. and +150° C.

C reacting, in the case where Y is NHCO, $R_2$ is halogen and X, $R_1$ and $R_3$ are as defined in general formula I above, a compound of formula D (D)

(I)

with a suitable halogenation agent such as $Br_2$, $Cl_2$, $I_2$, ICl, or $SO_2Cl_2$.

Thus, the reaction according to the process C may be carried out by aromatic electrophilic substitution using a suitable halogenation agent such as $Br_2$, $Cl_2$, $I_2$, ICl, or $SO_2Cl_2$. The reaction may be carried out using the salt or the base of the compound D in an appropriate solvent e.g. acetic acid, HCl/ethanol or water with or without a suitable base e.g. alkali metal acetate such as sodium acetate and at a reaction temperature between −20° C. and room temperature.

Working examples

Preparation of Intermediates and Starting Materials for the 5-$HT_{1B}$-antagonists Preparation 1

(R)-2-N,N-Dibenzylamino-8-methoxy-1,2,3,4-tetrahydronaphthalene

To a solution of (R)-8-methoxy-2-amino-1,2,3,4-tetrahydronaphthalene hydrochloride (24 g, 0.11 mol) in acetonitrile (600 mL) were added potassium carbonate (53 g, 0.39 mol), potassium iodide (catalytic amount) and benzyl bromide (34 mL, 0.28 mol). The reaction mixture was stirred at reflux for a period of 35 h. After the precipitate was filtered off and the acetonitrile removed in vacuo, the residue was partitioned between diethyl ether and water. The organic phase was separated, dried ($Na_2SO_4$) and evaporated in vacuo to give a crude product which was purified on a silica gel column using hexane/ethyl acetate, (3:1) as the eluent. Yield: 36 g (91%) of the title compound as a white solid: mp 105–107° C.; $[\alpha]^{21}_D$+124° (c 1.0, chloroform); EIMS (70 eV) m/z (relative intensity) 357 (100, $M^+$).

Preparation 2

(R)-7-N,N-Dibenzylamino-5,6,7,8-tetrahydro-1-naphthol (R)-2-N,N-Dibenzylamino-8-methoxy-1,2,3,4-tetrahydronaphthalene (43 g, 0.12 mol) was dissolved in diethyl ether (800 mL) and an excess of an ethereal HCl solution was added dropwise. The precipitate was filtered and dried in vacuo to give a white solid. This crude product (42 g, 0.11 mol) was dissolved in anhydrous methylene chloride (1 L) and cooled to −60° C. To the solution was boron tribromide (16 mL, 0.15 mol), dissolved in anhydrous methylene chloride (100 mL), added dropwise. The reaction temperature was allowed to reach −5° C. and was kept there overnight. To the ice-cooled solution was a 2 M aqueous ammonium hydroxide solution added dropwise and the mixture was extracted, twice, with methylene chloride. The combined organic phases were dried ($Na_2SO_4$), filtered and the solvent removed in vacuo to give a crude residue. Chromatography on silica (eluent: methylene chloride) gave 34 g (93% yield) of the title compound as a viscous clear oil: $[\alpha]^{21}_D$+118° (c 1.5, chloroform); EIMS (70 eV) m/z (relative intensity) 343 (53, $M^+$).

Preparation 3

(R)-2-(7-N,N-Dibenzylamino-5,6,7,8-tetrahydro-1-naphthyloxy)-2-methylpropanamide (R)-2-N,N-Dibenzylamino-5,6,7,8-tetrahydro-1-naphthol (10 g, 29 mmol) was stirred in anhydrous dioxane (150 mL) with sodium hydride (80% in oil, 0.96 g, 32 mmol) for 1 h. 2-Bromo-2-methylpropanamide (4.8 g, 29 mmol; described in: Coutts, I. G. C.; Southcott, M. R. *J. Chem. Soc. Perkin Trans. 1* 1990, 767–770) was added and the reaction mixture was heated at 100° C. for 2.5 h. After cooling, the precipitated sodium bromide was filtered off, the filtrate evaporated in vacuo and the residue was partitioned between water and methylene chloride. The organic phase was separated, dried ($Na_2SO_4$), filtered and evaporated to give a crude product which was purified on a silica gel column using methylene chloride as the eluent. Yield: 9.6 g (76%) of the title compound as white crystals: mp 125–126° C.; $[\alpha]^{21}_D$+98° (c 1.1, chloroform); EIMS (70 eV) m/z (relative intensity) 428 (13, $M^+$).

Preparation 4

(R)-N-(7-N,N-Dibenzylamino-5,6,7,8-tetrahydro-1-naphthyl)-2-hydroxy-2-methylpropanamide To a solution of (R)-2-(7-N,N-dibenzylamino-5,6,7,8-tetrahydro-1-naphthyloxy)-2-methylpropanamide (9.1 g, 21 mmol) in anhydrous 1,3-dimethyl-3,4,5,6-tetrahydro-2(1H)-pyrimidone (10 mL) and dry N,N-dimethylformamide (100 mL) was added sodium hydride (80% in oil, 1.4 g, 47 mmol) and the reaction was heated at 130° C. for 8 h. The solution was poured into a mixture of ice and water and extracted three times with ethyl acetate. The combined organic phases were dried ($Na_2SO_4$), filtered and evaporated in vacuo. Chromatography on silica (eluent: chloroform/ethanol saturated with $NH_3$; 100:0.5) gave 7.6 g (84% yield) as white crystals: mp 134–135° C.; $[\alpha]^{21}_D$+130° (c 1.1, chloroform); EIMS (70 eV) m/z (relative intesity) 428 (1, $M^+$).

Preparation 5
(R)-2-N,N-Dibenzylamino-8-amino-1,2,3,4-tetrahydronaphthalene (R)-N-(7-N,N-Dibenzylamino-5,6,7,8-tetrahydro--naphthyl)-2-hydroxy-2-methylpropionamide (7.4 g, 17 mmol) was dissolved in a mixture of ethanol (200 mL) and a 20% HCl aqueous solution (300 mL) and heated to reflux for 8 h. The ethanol was evaporated in vacuo and the remaining solution was washed twice with diethyl ether and cooled on ice-bath. After alkalization with a 45% aqueous solution of sodium hydroxide the mixture was extracted with methylene chloride. The combined organic phases were dried ($Na_2SO_4$), filtered and evaporated in vacuo. Purification on a silica gel column using chloroform as the eluent gave 3.8 g (76% yield) of the title compound as a light-brown oil: $[\alpha]^{21}_D$+124° (c 0.9, chloroform); EIMS (70 eV) m/z (relative intensity) 342 (92, $M^+$).

Preparation 6
(R)-1-(7-N,N-Dibenzylamino-5,6,7,8-tetrahydro-1-naphthyl)-4-N-methylpiperazine-2,6-dione 1,1'-Carbonyldiimidazole (6.0 g, 37 mmol) was added to a stirred suspension of methyliminodiacetic acid (2.7 g, 18 mmol) in anhydrous tetrahydrofuran (250 mL). The reaction mixture was heated at reflux for 1.5 h. (R)-2-N,N-Dibenzylamino-8-amino-1,2,3,4-tetrahydronaphthalene (5.7 g, 17 mmol) was then added and stirring at reflux was continued for 17 h. An additional amount of 1,1'-carbonyldiimidazole (2.9 g, 18 mmol) was added and heating at reflux was continued for another 17 h. The solvent was evaporated in vacuo and the crude product was purified on a silica gel column using chloroform/ethanol saturated with $NH_3$ (100:0.5) as the eluent. Yield: 6.6 g (87%) of the title compound as an oil: $[\alpha]^{21}_D$+90° (c 0.52, chloroform); EIMS (70 eV) m/z (relative intensity) 453 (8, $M^+$).

Preparation 7
(R)-2-N,N-Dibenzylamino-8-(4-methylpiperazin-1-yl)-1,2,3,4-tetrahydronaphthalene (R)-1-(7-N,N-Dibenzylamino-5,6,7,8-tetrahydro-1-naphthyl)-4-methylpiperazine-2,6-dione (1.4 g, 3.1 mmol) was added to a suspension of lithium aluminium hydride (0.57 g, 15 mmol) in anhydrous diethyl ether (70 mL). The reaction mixture was heated at reflux for 7 h. The reaction was quenched by the addition of water (0.60 mL), 15% aqueous sodium hydroxide (0.60 mL) and again water (1.8 mL). The mixture was filtered, dried ($Na_2SO_4$) and evaporated in vacuo. Purification on a silica gel column using chloroform/ethanol saturated with $NH_3$ (100:2) as the eluent gave 1.0 g (79% yield) of the title compound as a viscous oil: $[\alpha]^{21}_D$+53° (c 0.5, chloroform); EIMS (70 eV) m/z (relative intensity) 425 (2, $M^+$).

Preparation 8
(R)-5-Bromo-2-N,N-dibenzylamino-8-(4-methylpiperazin-1-yl)-1,2,3,4-tetrahydronaphthalene.

To a solution of (R)-2-N,N-dibenzylamino-8-(4-methylpiperazin-1-yl)-1,2,3,4-tetrahydronaphthalene (2.8 g, 6.5 mmol) and sodium acetate (6.8 g, 83 mmol) in acetic acid (100 mL) bromine (370 μL, 7.2 mmol) was added in one portion and the reaction was stirred for 5 min. The solvent was evaporated in vacuo and the remaining solid was partitioned between water and methylene chloride and cooled on ice-bath. The water phase was alkalized with 2 M aqueous solution of sodium hydroxide and the phases were separated. The organic phase was dried ($Na_2SO_4$), filtered and evaporated in vacuo to give a crude product which was purified on a silica gel column using chloroform/ethanol saturated with $NH_3$ (100:2) as the eluent. Yield: 2 g (61%) of a viscous brown oil: EIMS (70 eV) m/z (relative intensity) 503 and 505 (0.6, $M^+$)

Preparation 9
(R)-2-N,N-Dibenzylamino-8-(piperazin-1-yl)-1,2,3,4-tetrahydronaphthalene (R)-2-N,N-Dibenzylamino-8-amino-1,2,3,4-tetrahydronaphthalene (9.8 g, 39 mmol) and bis-(2-chloroethyl)amine hydrochloride (5.5 g, 32 mmol) was dissolved in n-butanol (80 mL). The reaction mixture was stirred at 100° C. and after 65 h the mixture was filtered and the solvent evaporated in vacuo. Purification on a silica gel column using chloroform/methanol/ concentrated ammonium hydroxide (95:5:0.5) as the eluent gave 6.0 g (51% yield) of the title compound as a viscous oil: $[\alpha]^{21}_D$+72° (c 1.0, chloroform); EIMS (70 eV) m/z (relative intensity) 411 (2, $M^+$).

Preparation 10
(R)-2-Amino-8-(piperazin-1-yl)-1,2,3,4-tetrahydronaphthalene

To a solution of (R)-2-N,N-dibenzylamino-8-(piperazin-1-yl)-1,2,3,4-tetrahydronaphthalene (5.5 g, 13 mmol) in methanol (400 mL) were added ammonium formate (20 g, 0.32 mol) and palladium (10%) on activated carbon (1.9 g). The mixture was refluxed for 1 h and the palladium was then filtered off. The solvent was evaporated in vacuo and the residue was partitioned between methylene chloride and a 2 M ammonium hydroxide solution. The organic phase was separated, dried ($Na_2SO_4$), filtered and evaporated in vacuo to give a crude product which was purified on a silica gel column using chloroform/ethanol/concentrated ammonium hydroxide (80:20:2.5) as the eluent. Yield: 2.4 g (76%) of the title compound as an oil: $[\alpha]^{21}_D$+9.9° (c 1.0, chloroform); EIMS (70 eV) m/z (relative intensity) 231 (24, $M^+$).

Preparation 11
(R)-2-Amino-5-bromo-8-(piperazin-1-yl)-1,2,3,4-tetrahydronaphthalene The title compound was prepared from (R)-2-amino-8-(piperazin-1-yl)-1,2,3,4-tetrahydronaphthalene following the general method of preparation 8. Purification on a silica gel column using methylene chloride/ethanol/concentrated ammonium hydroxide (80:20:2) as the eluent gave 0.8 g (67% yield) of a viscous light brown oil: $[\alpha]^{21}_D$–6.2° (c=1, chloroform); EIMS (70 eV) m/z (relative intensity) 309 and 311 (3.5, $M^+$)

Preparation 12
tert-Butyl (R)-4-(7-Amino-4-bromo-5,6,7,8-tetrahydro-1-naphthyl)piperazin-1-carboxylate To an ice-cooled solution of (R)-2-amino-5-bromo-8-(piperazin-1-yl)-1,2,3,4-tetrahydronaphthalene (0.8 g, 2.6 mmol) and triethylamine (0.53 mL, 3.9 mmol) in methylene chloride (50 mL) was added di-tert-butyl dicarbonate (0.56 g, 2.6 mmol) dissolved in methylene chloride (10 mL). After the addition, the reaction was allowed to stir at ambient temperature for 1 h. Water (10 mL) was added and the mixture was cooled on an ice-bath. The water phase was alkalized with a 2 M aqueous solution of sodium hydroxide and the phases were separated. The organic phase was dried ($Na_2SO_4$), filtered and evaporated in vacuo to give a crude product which was purified on a silica gel column using chloroform/methanol/concentrated ammonium hydroxide (95:5:0.5) as the eluent. Yield: 0.41 g (38%) of a viscous colorless oil: $[\alpha]^{21}_D +13°$ (c=1, chloroform); EIMS (70 eV) m/z (relative intensity) 409 and 411 (75, M$^+$)

Preparation 13

(R)-N-[5-Bromo-8-(4-tert-butyloxycarbonylpiperazin-1-yl)-1,2,3,4-tetrahydro-2-naphthyl]-4-morpholinobenzamide 4-Morpholinobenzoic acid (0.50 g, 2.4 mmol; described in: Degutis, J.; Rasteikiene, L.; Degutiene, A. Zh. *Org. Khim.* 1978, 14(10), 2060–2064) was dissolved in thionyl chloride (10 mL). After 2 min, the thionyl chloride was evaporated in vacuo and the residue was treated with toluene and again the solvent was evaporated in vacuo. Crude acid chloride (81 mg, 0.36 mmol) was dissolved in methylene chloride (10 mL) and added dropwise to a solution of tert-butyl (R)-4-(7-amino-4-bromo-5,6,7,8-tetrahydro-1-naphthyl)piperazin-1-carboxylate (140 mg, 0.34 mmol) and triethylamine (71 µL, 0.51 mmol) in methylene chloride (10 mL). After the addition, the reaction was stirred at ambient temperature for 15 min and was then washed with a diluted aqueous solution of sodium hydrogen carbonate and the phases were separated. The organic phase was dried ($Na_2SO_4$), filtered and evaporated in vacuo and the residue was purified on a silica gel column using chloroform/ethanol saturated with $NH_3$ (100:2) as the eluent. Yield: 160 mg (79%) of a viscous colorless oil: $[\alpha]^{21}_D -11°$ (c=1, chloroform); TSPMS m/z (relative intensity) 599 and 601 (35, M$^+$+1).

Preparation 14

(R)-2-Amino-8-(4-methylpiperazin-1-yl)-1,2,3,4-tetrahydronaphthalene

To a solution of (R)-2-N,N-dibenzylamino-8-(4-methylpiperazin-1-yl)-1,2,3,4-tetrahydronaphthalene (4.0 g, 9.4 mmol) in methanol (250 mL) were added ammonium formate (14 g, 56 mmol) and palladium (10%) on activated carbon (1.4 g). The mixture was refluxed for 3 h and the palladium was then filtered off. The solvent was evaporated in vacuo and the residue was partitioned between methylene chloride and a 2 M ammonium hydroxide solution. The organic phase was separated, dried ($Na_2SO_4$), filtered and evaporated in vacuo to give a crude product which was purified on a silica gel column using chloroform/methanol/concentrated ammonium hydroxide (90:9:0.5) as the eluent. Yield: 1.9 g (83%) as an oil: $[\alpha]^{21}_D -2.7°$ (c 1.0,chloroform); EIMS (70 eV) m/z (relative intensity) 245 (5, M$^+$).

Preparation 15

(R)-2-Amino-5-bromo-8-(4-methylpiperazin-1-yl)-1,2,3,4-tetrahydronaphthalene

The title compound was prepared from (R)-2-amino-8-(4-methylpiperazin-1-yl)-1,2,3,4-tetrahydronaphthalene following the general method of Preparation 8. Purification on a silica gel column using chloroform/ethanol/concentrated ammonium hydroxide (80:20:2) as the eluent gave 630 mg (89% yield) of a viscous colorless oil: EIMS (70 eV) m/z (relative intensity) 323 and 325 (20, M$^+$)

Preparation 16

(R)-2-Amino-8-bromo-5-methoxy-1,2,3,4-tetrahydronaphthalene Hydrochloride (R)-2-Amino-5-methoxy-1,2,3,4-tetrahydronaphthalene hydrochloride (5.0 g, 23 mmol) was dissolved in acetic acid (300 mL) under nitrogen atmosphere. Sodium acetate (5.5 g, 70 mmol) was added and bromine (3.5 g, 23 mmol) was then added in one portion. The mixture was stirred for 5 minutes at room temperature. The solvent was removed in vacuo to give a solid residue which was partitioned between ethyl acetate and NaOH (2 M). The layers were separated and the aqueous phase was extracted twice with ethyl acetate. The organic layers were combined and dried ($Na_2SO_4$). The solvent was removed in vacuo to give a brown oily residue. The HCl salt was precipitated from diethyl ether/methylene chloride by the addition of HCl in diethyl ether (3 M): yield 7.7 g (94%). Recrystallization from methanol gave the title compound as needle crystals: mp 264–265° C.; $[\alpha]^{21}_D +54°$ (c 1, MeOH); ELMS (70 eV) m/z (relative intensity) 257 (30, M$^+$, $^{81}$Br), 255 (31, M$^+$, $^{79}$Br).

Preparation 17

(R)-8-Bromo-2-N,N-dibenzylamino-5-methoxy-1,2,3,4-tetrahydronaphthalene (R)-2-Amino-8-bromo-5-methoxy-1,2,3,4-tetrahydronaphthalene hydrochloride (4.5 g, 17.5 mmol), benzyl bromide (6.6 g, 38 mmol), potassium carbonate (9.7 g, 70 mmol) and potassium iodide (100 mg, catalytic amount) were mixed with acetonitrile (250 mL) under nitrogen atmosphere and refluxed for 18 h. The solvent was removed in vacuo and the residue was partitioned between ethyl acetate and ammonia (2 M). The layers were separated and the organic layer was dried ($MgSO_4$). The solvent was removed in vacuo to give a residue which was purified by flash chromatography on silica gel using hexane/methylene chloride 8:2 as the eluent. The title compound was obtained as an oil. Yield 7.5 g (98% ): $[\alpha]^{21}_D +87°$ (c 1, MeOH); EIMS (70 eV) m/z (relative intensity) 437 (12, M$^+$,$^{81}$Br), 435 (13, M$^+$,$^{79}$Br).

Preparation 18

(R)-2-N,N-Dibenzylamino-5-methoxy-8-(4-methylpiperazin-1-yl)-1,2,3,4-tetrahydronaphthalene To a solution of (R)-8-bromo-2-N,N-dibenzylamino-5-methoxy-1,2,3,4-tetrahydronaphthalene (19 g, 44 mmol) in dry toluene (500 mL) under an argon atmosphere was added N-methylpiperazine (5.9 mL, 53 mmol), tris(dibenzylideneacetone)dipalladium(0) (0.41 g, 0.44 mmol), (R)-BINAP (0.82 g, 1.3 mmol) and sodium tert-butoxide (0.40 mg, 4.2 mmol). The dark solution was stirred at 85° C. for 23 h and was then cooled, filtered and evaporated in vacuo. Purification on a silica gel column using chloroform/ethanol saturated with $NH_3$ (100:2) as the eluent gave 19 g (97% yield) of a viscous colorless oil: $[\alpha]^{21}_D +72°$ (c=1, chloroform); EIMS (70 eV) m/z (relative intensity) 455 (15, M$^+$).

Preparation 19

(R)-2-Amino-5-methoxy-8-(4-methylpiperazin-1-yl)-1,2,3,4-tetrahydronaphthalene

The title compound was prepared from (R)-2-N,N-dibenzylamino-5-methoxy-8-(4-methylpiperazin-1-yl)-1,2,3,4-tetrahydronaphthalene following the general method of Preparation 10. Yield: 5.3 g (82%) of a viscous colorless oil: $[\alpha]^{21}_D +20°$ (c=1.1, chloroform); EIMS (70 eV) m/z (relative intensity) 275 (53, M$^+$).

Preparation 20

Methyl 5-Methoxy-8-nitro-1,2,3,4-tetrahydronaphthalene-2-carboxylate

Methyl 5-methoxy-1,2,3,4-tetrahydronaphthalene-2-carboxylate (1.1 g, 5 mmol; described in: Johnson, D. W.; Mander, L. N. *Aust.J.Chem.* 1974, 8, 1277–1286) dissolved in acetic anhydride (20 mL), was treated with 70% nitric acid (0.4 mL) at 0° C. for 1 h and the mixture was poured into ice-water and diethyl ether. The organic phase was separated, evaporated in vacuo and the residue triturated with diisopropyl ether to yield 0.27 g (20%) of the title compound as crystals: mp 100–104° C.; EIMS (70 eV) m/z (relative intensity) 265 (35, M$^+$).

Preparation 21
5-Methoxy-8-nitro-1,2,3,4-tetrahydronaphthalene-2-carboxylic Acid A mixture of methyl 5-methoxy-8-nitro-1,2,3,4-tetrahydronaphthalene-2-carboxylate (1.9 g, 7.1 mmol) in methanol (20 mL) and 2 M NaOH (10 mL) was refluxed for 1.5 h and the solvent was evaporated in vacuo. The residue was taken up in ethyl acetate and acidified. The organic phase was separated and dried and evaporated in vacuo to afford 1.7 g (95% yield) of crystals: mp (after recrystallization in diisopropyl ether/ethanol) 189–190° C.; EIMS (70 eV) m/z (relative intensity) 251 (30, M$^+$).

Preparation 22
N-(4-Morpholinophenyl)-5-methoxy-8-nitro-1,2,3,4-tetrahydronaphthalene-2-carboxamide A mixture of 5-methoxy-8-nitro-1,2,3,4-tetrahydronaphthalene-2-carboxylic acid (1.3 g, 5 mmol), toluene (20 mL) and thionyl chloride (1.8 mL, 25 mmol) was heated at 80° C. for 1 h. The solvents were removed in vacuo and the residue, dissolved in methylene chloride (10 mL), was added to a solution of 4-morpholinoaniline (890 mg, 5 mmol) and triethylamine (1.0 g, 10 mmol) in methylene chloride (20 mL) at 0° C. The mixture was stirred at 20° C. for 2 h, water was added and the precipitate was filtered to yield 1.9 g (90%) of the title product as crystals: mp 251–253° C.; EIMS (70 eV) m/z (relative intensity) 411 (100, M$^+$).

Preparation 23
N-(4-Morpholinophenyl)-8-amino-5-methoxy-1,2,3,4-tetrahydronaphthalene-2-carboxamide A solution of N-(4-morpholinophenyl)-5-methoxy-8-nitro-1,2,3,4-tetrahydronaphthalene-2-carboxamide (2.05 g, 5 mmol) and sodium dithionite (3.5 g, 20 mmol) in N,N-dimethylformamide (20 mL) and water (2 mL) was heated at 90° C. for 7 h. After cooling, the reaction mixture was partitioned between water and ethyl acetate, the phases were separated and the organic phase was washed, twice, with water and evaporated in vacuo. The residue was triturated with diisopropyl ether/ethyl acetate affording 1.4 g (72% yield) of the title product as crystals: mp 219–222° C.; EIMS (70 eV) m/z (relative intensity) 381 (70, M$^-$).

Preparation 24
N-(4-Morpholinocarbonylphenyl)-5-methoxy-8-nitro-1,2,3,4-tetrahydronaphthalene-2-carboxamide A mixture of 5-methoxy-8-nitro-1,2,3,4-tetrahydronaphthalene-2-carboxylic acid (1.0 g, 4 mmol), toluene (20 mL), N,N-dimethylformamide (10 drops) and thionyl chloride (1.5 mL, 20 mmol) was heated at 60° C. for 1 h. The solvents were removed in vacuo and the residue, dissolved in methylene chloride (20 mL), was added to a solution of 4-aminobenzoylmorpholine (820 mg, 4 mmol, described in: Devlin J. P. *J.Chem.Soc.* Perkin Trans I, 1975, 830–841) and triethylamine (800 mg, 8 mmol) in methylene chloride (30 mL) at 5° C. After stirring at 20° C. for 2 h, water was added and the organic phase was separated, dried and the solvent removed in vacuo. The oily residue was crystallized from diisopropyl ether/ethyl acetate affording 1.2 g (73% yield) of the title compound as crystals: mp 186–189° C.; EIMS (70 eV) m/z (relative intensity) 439 (20, M$^+$).

Preparation 25
N-(Morpholinocarbonylphenyl)-8-amino-5-methoxy-1,2,3,4-tetrahydronaphthalene-2-carboxamide A solution of N-(4-morpholinocarbonylphenyl)-5-methoxy-8-nitro-1,2,3,4-tetrahydronaphthalene-2-carboxamide (1.3 g, 2.8 mmol) and sodium dithionite (2.0 g, 11 mmol) in N,N-dimethylformamide (20 mL) and water (2.5 mL) was heated at 85° C. for 3 h. After cooling, the reaction mixture was partitioned between water and ethyl acetate, the phases were separated and the organic phase was washed, twice, with water and evaporated in vacuo. The organic phase was dried and evaporated. The residue was treated with diisopropyl ether affording 310 mg (30% yield) of the title product as crystals: EIMS (70 eV) m/z (relative intensity) 409 (100, M$^+$).

Preparation 26
(R)-2-N,N-Dibenzylamino-5-(1-hydroxyethyl)-8-(4-methylpiperazin-1-yl)-1,2,3,4-tetrahydronaphthalene (R)-5-Bromo-2-N,N-dibenzylamino-8-(4-methylpiperazin-1-yl)-1,2,3,4-tetrahydro-naphthalene (1.4 g, 2.8 mmol) was dissolved in freshly distilled tetrahydrofuran (100 mL), flushed with argon and cooled to –78° C. To the solution was added tert-butyl lithium (2.6 mL, 1.4 M in pentane, 3.7 mmol) and the reddish solution was stirred at ambient temperature for 10 min. Acetaldehyde (320 µL, 5.7 mmol) was added and the reaction mixture was stirred at –78° C. for 10 min, at 0° C. for 2 h and at room temperature for 10 min. The reaction was quenched with water and the solvent was evaporated in vacuo. The residue was partitioned between diethyl ether (100 mL) and 2 M NH$_3$ (20 mL) and the aqueous phase was extracted with diethyl ether (20 mL). The combined organic layers were washed with brine (20 mL) and dried (MgSO$_4$). The solvent was evaporated giving 2.0 g of a crude product. Purification by column chromatography on silica gel using chloroform/methanol/conc. NH$_3$ (95:5:0.5) as the eluent gave 910 mg (68% yield) of the title compound as a yellowish foam: ESI m/z (relative intensity) 470 (100, M+1).

Preparation 27
(R)-2-Amino-5-ethyl-8-(4-methylpiperazin-1-yl)-1,2,3,4-tetrahydronaphthalene (R)-2-N,N-Dibenzylamino-5-(1-hydroxyethyl)-1,2,3,4-tetrahydronaphthalene (1.6 g, 3.4 mmol) was dissolved in acetic acid (80 mL) and stirred at 100° C. for 2 h. The solvent was evaporated in vacuo and the residue was dissolved in methanol (150 mL). Palladium (10%) on charcoal (600 mg) was added and the solution was flushed with nitrogen. To the solution was added ammonium formate (1.7 g, 28 mmol) and the reaction mixture was stirred at 65° C. for 2 h. The catalyst was filtered off and the solvent was evaporated in vacuo giving 1.3 g of a crude product. The residue was partitioned between methylene chloride (120 mL) and 2 M NH$_3$ (30 mL). The organic phase was washed with brine (20 mL) and dried (MgSO$_4$). The solvent was evaporated in vacuo giving 740 mg (79% yield) of the title compound as a white semi-crystalline solid: EIMS (70 eV) m/z (relative intensity) 273 (24, M$^+$).

Preparation 28
(R-N-[8-(4-Methylpiperazin-1-yl)-1,2,3,4-tetrahydro-2-naphthyl]-4-trifluoromethylbenzamide To an ice-cooled solution of (R)-2-amino-8-(4-methylpiperazin-1-yl)-1,2,3,4-tetrahydronaphthalene (110 mg, 0.44 mmol) and triethylamine (91 µL, 0.66 mmol) in methylene chloride (20 mL) was 4-(trifluoromethyl)benzoyl chloride (96 mg, 0.46 mmol) in methylene chloride (5 mL) added dropwise. After the addition the reaction was allowed to stir at ambient temperature for 15 min and was then washed with diluted aqueous sodium hydrogen carbonate. The phases were separated and the organic phase was dried (Na$_2$SO$_4$), filtered and evaporated in vacuo to give a crude product which was purified on a silica gel column using chloroform/ethanol saturated with NH$_3$ (100:2) as the eluent. Yield: 150 mg (81%) of the title compound as white crystals: mp 203–204° C.; $[\alpha]^{21}{}_D$–b 20° (c 1.0, chloroform); EIMS (70 eV) m/z (relative intensity) 417 (10, M$^+$).

Preparation 29
(R)-2-N,N-Dibenzylamino-5-hydroxymethyl-8-(4-methylpiperazin-1-yl)-1,2,3,4-tetrahydronaphthalene (R)-5-Bromo-2-N,N-dibenzylamino-8-(4-methylpiperazin-1-yl)-1,2,3,4-tetrahydronaphthalene (800 mg, 1.6 mmol) was dissolved in freshly distilled tetrahydrofuran (80 mL), flushed with argon and cooled to −78° C. To the solution was added tert-butyl lithium (1.5 mL, 1.4 M in pentane, 2.1 mmol) and the reaction mixture was stirred at ambient temperature for 10 min. Methyl chloroformate (250 µL, 3.2 mmol) was added and the reaction mixture was stirred at −78° C. for 50 min and at 0° C. for 1 h. The reaction was quenched with water and the solvent was evaporated in vacuo. The residue was partitioned between diethyl ether (90 mL) and 2 M $NH_3$ (15 mL). The organic layer was washed with brine (10 mL) and dried ($MgSO_4$). The solvent was evaporated in vacuo giving 770 mg of a crude product. Purification by column chromatography on silica gel using chloroform/methanol/conc. $NH_3$ (250:5:0.5) as the eluent afforded 610 mg of (R)-5-carboxymethyl-2-N,N-dibenzylamino-8-(4-methylpiperazin-1-yl)-1,2,3,4-tetrahydronaphthalene (containing 13% of the corresponding 5-hydrogen analogue) as a yellowish oil: EIMS (70 eV) m/z (relative intensity) 483 (1, M$^+$). The methyl ester (610 mg, 1.1 mmol) was dissolved in freshly distilled tetrahydrofuran (35mL) and lithium aluminum hydride (120 mg, 3.1 mmol) was added. The reaction mixture was stirred at 45° C. for 2 h followed by cooling to room temperature. The reaction was quenched with water (120 µL), 15% NaOH (120 µL) and water (240 µL) followed by stirring the slurry at room temperature for 2.5 h. The precipitate was filtered off and the solvent was evaporated in vacuo giving 730 mg of a crude product. Purification by column chromatography on a silica gel column using chloroform/methanol/conc. $NH_3$ (95:5:0.5) as the eluent gave 360 mg (50% yield) of the title compound as a white foam: EIMS (70 eV) m/z (relative intensity) 455 (1, M$^+$); $[\alpha]^{21}_D$+44° (c 0.12, chloroform).

Preparation 30
(R)-2-Amino-5-methyl-8-(4-methylpiperazin-1-yl)-1,2,3,4-tetrahydronaphthalene (R)-2-N,N-Dibenzylamino-5-hydroxymethyl-8-(4-methylpiperazin-1-yl)-1,2,3,4-tetrahydronaphthalene (360 mg, 0.78 mmol) was dissolved in methanol (35 mL), palladium (10%) on charcoal (170 mg) was added and the solution was flushed with nitrogen. To the solution was added ammonium formate (390 mg, 6.2 mmol) and the reaction mixture was stirred at 65° C. for 13 h. The catalyst was filtered off and the solvent was evaporated in vacuo giving 220 mg of a residue. The crude hydroxymethyl compound was dissolved in acetic acid (25 mL), palladium (10%) on charcoal (60 mg) was added and the solution was flushed with hydrogen. The reaction mixture was hydrogenated at room temperature and at atmospheric pressure for 4 h. The catalyst was filtered off and more palladium (10%) on charcoal (160 mg) was added followed by hydrogenation at room temperature and at atmospheric pressure for 24 h. The catalyst was filtered off and the solvent was evaporated in vacuo. The residue was partitioned between diethyl ether (70 mL) and conc. $NH_3$ and the organic phase was washed with brine (5 mL). The organic layer was dried ($MgSO_4$) and the solvent was evaporated in vacuo to give 120 mg (61% yield) of the title compound as a white semi-crystalline solid: EIMS m/z (relative intensity) 259 (20, M$^+$); $[\alpha]^{21}_D$−1° (c 0.09, chloroform).

Preparation 31
(S)-3-N,N-Dibenzylamino-5-methoxy-3,4-dihydro-2H-1-benzopyran hydrochloride.

(S)-3-Amino-5-methoxy-3,4-dihydro-2H-1-benzopyran (45 g, 0.25 mol; described in WO 93/07135), $K_2CO_3$ (120 g, 0.87 mol) and benzylbromide (65 mL, 0.55 mol) were mixed in acetonitrile (1000 mL) under nitrogen. The reaction mixture was refluxed for 45 h. The mixture was filtered and the solvent was removed in vacuo, and the residue was partitioned between diethyl ether and saturated NaCl (aq). The layers were separated and the organic phase was dried ($MgSO_4$) and filtered followed by precipitation of the hydrochloric salt at room temperature. Yield: 99 gram (99%). An analytical sample was transferred to the base: $[\alpha]^{21}_D$+116° (c 1.0, chloroform). EIMS (70 eV) m/z (relative intensity) 359 (28, M$^+$).

Preparation 32
(S)-3-N,N-Dibenzylamino-5-hydroxy-3,4-dihydro-2H-1-benzopyran.

(S)-3-N,N-Dibenzylamino-5-methoxy-3,4-dihydro-2H-1-benzopyran hydrochloride (67 g, 0.17 mol) was dissolved in methylene chloride (500 mL) under nitrogen, and the solution was cooled to −75° C. Boron tribromide (32 mL, 0.34 mol) was added dropwise over 5 min. The temperature was then allowed to slowly reach +5° C., and the reaction was stirred over night. The reaction mixture was carefully quenched with an 2 M aqueous solution of $NH_3$ under stirring. The layers were separated and the aqueous phase was extracted two times with methylene chloride. The organic layers were combined, washed with brine, dried ($MgSO_4$), filtered and the solvent was removed in vacuo to give a brownish oily residue which was purified by flash chromatography on a silica gel column using methylene chloride as the eluent. Yield: 50 g (86%) of the title compound: $[\alpha]^{21}_D$+109° (c 1.0, chloroform); EIMS (70 eV) m/z (relative intensity) 345 (5, M$^+$).

Preparation 33
(S)-2-(3-N,N-Dibenzylamino-3,4-dihydro-2H-1-benzopyran-5-yloxy)-2-methylpropanamide.

(S)-3-N,N-Dibenzylamino-5-hydroxy-3,4-dihydro-2H-1-benzopyran (50 g, 0.14 mol) was dissolved in anhydrous 1,4-dioxane (450 mL) under nitrogen. A dispersion of sodium hydride (60–65% in oil, 6.1 g, 0.15 mol) was added in portions. The mixture was stirred for 1 h at room temperature. 2-Bromo-2-methylpropanamide (24 g, 0.14 mol; Coutts, I. G. C.; Southcott, M. R. *J. Chem. Soc. Perkin Trans. 1* 1990, 767–771) was added to the dark greenish solution and was heated at reflux with stirring for 3 h. An additional amount of sodium hydride (60–65% in oil, 2.8 g, 70 mmol) and 2-bromo-2-methylpropanamide (4.6 g, 28 mmol) was added in portions and heating at 60° C. was continued for 17 h. After cooling, a small amount of methanol (10 mL) was added and the solution was filtered and the solvent was removed in vacuo. The residue was partitioned between ethyl acetate (500 mL) and a saturated $NaHCO_3$ solution (50 mL). The organic layer was dried ($MgSO_4$), and the solvent was removed in vacuo to give a brownish residue which was crystallized from ethyl acetate/hexane. Yield: 45 g (71%) of the title compound as a white solid: mp 133–134° C.; $[\alpha]^{21}_D$+99° (c 1.0, chloroform).; EIMS (70 eV) m/z (relative intensity) 430 (9, M$^+$).

Preparation 34
(S)-5-Amino-3-N,N-dibenzylamino-3,4-dihydro-2H-1-benzopyran.

To a solution of (S)-2-(3-N,N-dibenzylamino-3,4-dihydro-2H-1-benzopyran-5-yloxy)-2-methylpropanamide (46 g, 0.11 mol) in anhydrous N,N-dimethylformamide (450 mL) and 1,3-dimethyl-3,4,5,6-tetrahydro-2(1H)-pyrimidinone (45 mL) was added sodium hydride (60–65% in oil, 8.5 g, 0.21 mol) in portions under nitrogen. The reaction mixture was heated at 110° C. with stirring for 13 h. The mixture was then allowed to cool, and the solution was partitioned between ethyl acetate (400 mL) and a 2 M $NH_3$ solution (200 mL). The layers were separated, and the aqueous layer was extracted with ethyl acetate (150 mL). The combined organic layers were dried ($MgSO_4$) and concentrated in vacuo to give a brownish oil. EIMS (70 eV) m/z (relative intensity) 430 (3, M$^+$). The obtained material (0.11 mol) was dissolved in ethanol (350 mL). A 6 M HCl solution (250 mL) was added, and the reaction mixture was heated at reflux for 16 h. After stirring, the mixture was allowed to cool to 35° C., the ethanolic solvent was removed in vacuo, and ethyl acetate was added to the aqueous remains. The mixture was cooled on ice, and a solution of conc. $NH_3$ was slowly added with stirring. The layers were separated, and the aqueous layer was extracted with another portion of ethyl acetate. The combined organic layers were dried ($MgSO_4$), and the solvent was removed in vacuo to give a brownish oil which was purified on a short column of silica gel (eluent: hexane/ethyl acetate; 8:2) affording 25 g (68% yield) of the desired compound as a light yellow oil. The product slowly crystallized upon standing in the refrigerator. An analytical sample was recrystallized from diethyl ether/petroleum ether: mp 101–103° C.; $[\alpha]^{21}_D$+123° (c 1.0, chloroform); EIMS (70 eV) m/z (relative intensity) 344 (17, M$^+$).

Preparation 35
(S)-1-(3-N,N-Dibenzylamino-3,4-dihydro-2H-1-benzopyran-5-yl)-4-methylpiperazine-2,6-dione.

To a dispersion of N-methyliminodiacetic acid (6.90 g, 46.9 mmol) in anhydrous tetrahydrofuran (575 mL) was added 1,1'-carbonyldiimidazole (15.2 g, 93.9 mmol), and the mixture was heated at reflux for 2 h under nitrogen. A solution of (S)-5-amino-3-N,N-dibenzylamino-3,4-dihydro-2H-1-benzopyran (15.0 g, 42.7 mmol) in tetrahydrofuran (120 mL) was added with stirring over 0.5 h. The reaction mixture was heated at reflux for 28 h, then allowed to cool, and the solvent was removed in vacuo. The residue was purified on a short column of silica gel (eluent: methylene chloride and ethyl acetate) affording 14.1 g (71% yield) of the title compound as a light yellow solid: mp sinters>60° C.; $[\alpha]^{21}_D$+89° (c 1.0, chloroform); EIMS (70 eV) m/z (relative intensity) 455 (8, M$^+$).

Preparation 36
(S)-3-N,N-Dibenzylamino-5-(4-methylpiperazin-1-yl)-3,4-dihydro-2H-1-benzopyran.

To a stirred solution of (S)-1-(3-N,N-dibenzylamino-3,4-dihydro-2H-1-benzopyran-5-yl)-4-methylpiperazine-2,6-dione (25.4 g, 55.8 mmol) in anhydrous diethyl ether (800 mL) was added lithium aluminum hydride (9.30 g, 246 mmol) in portions. The reaction mixture was heated to reflux for 6.5 h under nitrogen and was stirred over night at room temperature. The mixture was cooled (ice-bath), and water (10 mL) was added followed by a 15% aqueous solution of NaOH (10 mL) and another portion of water (30 mL). The precipitate was filtered off and washed with several portions of warm tetrahydrofuran. The organic layers were combined, and the solvent was removed in vacuo. The residue was purified by column chromatography on silica (eluent: chloroform/ethanol; 95:5+0.5% conc. $NH_3$) affording 13.6 g (57% yield) of the title compound as a light yellow oil: $[\alpha]^{25}_D$+63° (c 1.0, methanol); EIMS (70 eV) m/z (relative intensity) 427 (5, M$^+$).

Preparation 37
(S)-3-Amino-5-(4-methylpiperazin-1-yl)-3,4-dihydro-2H-1-benzopyran.

To a solution of (S)-3-N,N-dibenzylamino-5-(4-methylpiperazin-1-yl)-3,4-dihydro-2H-1-benzopyran (2.6 g, 6.2 mmol) in anhydrous methanol (100 mL) were added palladium (10%) on activated carbon (0.97 g) and ammonium formate (3.1 g, 49 mmol) under nitrogen. The reaction mixture was heated at 50° C. with stirring overnight. The solution was filtered through Celite®, and the solvent was removed in vacuo. The residue was partitioned between a 2 M $NH_3$ solution (20 mL) and ethyl acetate (100 mL). The layers were separated, and the aqueous layer was extracted with ethyl acetate (3×50 mL). The combined organic phases were dried ($Na_2SO_4$), and the solvent was removed in vacuo to give 1.4 g (89% yield) of the title compound as a pale yellow oil: $[\alpha]^{21}_D$–15° (c 1.0, chloroform); EIMS (70 eV) m/z (relative intensity) 247 (74, M$^+$).

Preparation 38
4-(4-Piperidon-1-yl)benzoic Acid.

A solution of 2 M NaOH (10 mL), 4-(8-aza-1,4-dioxaspiro[4,5]dec-8-yl)benzonitrile (820 mg, 3.36 mmol; described in: Taylor E. C.; Skotnicki J. S. *Synthesis* 1981, 8, 606–608), and ethanol (7.5 mL) was heated at reflux for 3 h. The external heating was interrupted, and the reaction mixture was stirred overnight at ambient temperature. The ethanolic solvent was removed in vacuo, and the remains were acidified to pH 4 with a 2 M HCl solution followed by extraction with ethyl acetate (50 mL). The layers were separated, and pH was adjusted to pH 6 with a 2 M NaOH solution followed by another extraction with ethyl acetate (50 mL). The combined organic layers were concentrated in vacuo, and the solid residue was dissolved in a 6 M HCl solution (10 mL). The reaction mixture was heated at 75° C. for 2.5 h and then at 55° C. overnight. The temperature was raised to 75° C. for 2 h, and the reaction mixture was then allowed to cool. The pH was adjusted to pH 4, and the solution was extracted with ethyl acetate (50 mL). The layers were separated, and another extraction was made at pH 5. The combined organic layers were dried ($MgSO_4$), and the solvent was removed in vacuo. The crude product was recrystallized from ethyl acetate affording 300 mg (41% yield) of the title compound as yellowish crystals: mp sinters>215 ° C.; EIMS (70 eV) m/z (relative intensity) 219 (100, M$^+$)

Preparation 39
(S)-3-N,N-Dibenzylamino-8-iodo-5-(4-methylpiperazin-1-yl)-3,4-dihydro-2H-1-benzopyran (S)-3-N,N-Dibenzylamino-5-(4-methylpiperazin-1-yl)-3,4-dihydro-2H-1-benzo-1-pyran (6.9 g, 16 mmol) and sodium acetate (1.5 g, 18 mmol) were dissolved in acetic acid (430 mL). To the solution was added iodine monochloride (18 mL, 1 M, 18 mmol) and the reaction mixture was stirred at room temperature, protected from light, for 24 h. Additional iodine monochloride (2.5 mL, 1M, 2.5 mmol) was added followed by stirring for 3 h. The solvent was evaporated in vacuo and the residue was partitioned between methylene chloride (800 mL) and 2 M NaOH (120 mL). The aqueous phase was extracted with methylene chloride (100 mL) and the combined organic layers were washed with brine (2×100 mL) and dried ($MgSO_4$). Evaporation of the solvent gave 8.6 g of a crude product. Purification by column chromatography on silica using ethyl acetate/ethanol (saturated with ammonia) (25:1) as the eluent gave 4.1 g (43% yield) of the title compound (containing about 7% of the starting material) as a yellowish solid: EIMS (70 eV) m/z (relative intensity) 553 (15, M$^+$). The product was used in the next step without further attempts to purification.

Preparation 40
(S)-8-Carboxymethyl-3-N,N-dibenzylamino-5-(4-methylpiperazin-1-yl)-3,4-dihydro-2H-1-benzopyran (S)-3-N, N-Dibenzylamino-8-iodo-5-(4-methylpiperazin-1-yl)-3,4-dihydro-2H-1-benzopyran (2.6 g, 4.8 mmol) was dissolved in N,N-dimethylformamide (100 mL) and flushed with carbonmonoxide. To the solution was added palladium acetate (110 mg, 0.48 mmol), 1,3-bis(diphenylphosphino) propane (200 mg, 0.48 mmol), methanol (25 mL) and triethylamine (3.3 mL, 24 mmol). The mixture was reacted with carbonmonoxide at 90° C. and at atmospheric pressure for 8 h. The solution was filtered, the solvent was evaporated. The residue was co-evaporated with xylene (2×50 mL) and partitioned between methylene chloride (300 mL) and 2 M $NH_3$ (50 mL). The aqueous phase was extracted with methylene chloride (50 mL) and the combined organic layers were washed with brine (2× 50 mL) dried ($MgSO_4$). The solvent was evaporated giving 4.0 g of a crude product. Purification by column chromatography on silica using methylene chloride/ethanol (saturated with ammonia) (50:1) as the eluent gave 1.7 g (68% yield) of the title compound (containing about 5% of the corresponding 8-H analogue) as a yellowish solid: EIMS (70 eV) m/z (relative intensity) 485 (8, $M^+$). The product was used in the next step without futher attempts to purification.

Preparation 41
(S)-3-N,N-Dibenzylamino-8-hydroxymethyl-5-(4-methylpiperazin-1-yl)-3,4-dihydro-2H-1-benzopyran (S)-8-Carboxymethyl-3-N,N-dibenzylamino-5-(methylpiperazin-1-yl)-3,4-dihydro-2H-1-benzopyran (490 mg, 1.0 mmol) was dissolved in dry tetrahydrofuran (40 mL) and lithium aluminium hydride (76 mg, 2.0 mmol) was added portionwise. The reaction mixture was stirred at 45° C. for 4 h and cooled to room temperature. The reaction was quenched by the addition of water (76 μL), 15% NaOH (76 [L) and water (225 μL) and stirred for 18 h. The white precipitate was filtered off and the solution was dried ($MgSO_4$). The solvent was evaporated in vacuo giving 520 mg of a crude product. Purification by column chromatography on silica using chloroform/ethanol (saturtated with ammonia) (15:1) as the eluent gave 390 mg (85% yield) of the title compound containing about 8% of the corresponding 8-methyl analogue) as a yellowish oil: EIMS (70 eV) m/z (relative intensity) 457 (15, $M^+$).

Preparation 42
(S)-3-Amino-8-methyl-5-(4-methylpiperazin-1-yl)-3,4-dihydro-2H-1-benzopyran (S)-3-N,N-Dibenzylamino-8-hydroxymethyl-5-(4-methylpiperazin-1-yl)-3,4-dihydro-2H-1-benzopyran (420 mg, 0.90 mmol) was dissolved in methanol (60 mL) and ammonium formate (460 mg, 7.3 mmol) was added. The solution was flushed with nitrogen and palladium on charcoal (120 mg, 10%) was added. The reaction mixture was stirred at 50 ° C. for 16 h. The catalyst was filtered off and the solvent was evaporated in vacuo giving 260 mg of a crude product. The residue was dissolved in acetic acid (50 mL) and palladium on charcoal (120 mg, 10%) was added. The reaction mixture was hydrogenated at room temperature and at atmospheric pressure for 46 h. The catalyst was filtered off and the solvent was evaporated in vacuo. The residue was partitioned between ethyl acetate (120 mL) and 2 M NaOH (10 mL) and the aqueous phase was extracted with ethyl acetate (10 mL). The combined organic layers were washed with brine (5 mL), dried ($MgSO_4$) and the solvent was evaporated in vacuo giving 200 mg, of a crude product. Purification by preparative TLC on silica using chloroform/ethanol (saturated with ammonia) (10:1) as the eluent afforded 150 mg (64% yield) of the title compound as an oil: EIMS (70 eV) m/z (relative intensity) 261 (100, $M^+$).

Preparation 43
8-Methoxy-5-nitro-3,4-dihydro-2H-1-benzopyran-3-carboxylic acid ethyl ester.

To a stirred solution of 8-methoxy-3,4-dihydro-2H-1-benzopyran-3-carboxylic acid ethyl ester (5.5 g, 23 mmol; described in: Thorberg, S-O et al. *Acta Pharm.Suec.*1987, 24, (4), 169–182 ) in methylene chloride (50 mL) at 0° C. was added dropwise 65% $HNO_3$ (2.0 mL). The solution was stirred at room temperature for 2 h and washed with water. The organic phase was dried and the solvent evaporated in vacuo. The residue was treated with diisopropyl ether (30 mL) and ethyl acetate (5 mL) to yield 1.5 g (5.3 mmol) of crystals of the 6-nitro isomer. The mother liquor was purified by column chromatography using diisopropylether as the eluent affording 1.3 g (20% yield) of the title compound: mp 66–68° C.; EIMS (70 eV) m/z (relative intensity) 281 (100, $M^+$).

Preparation 44
8-Methoxy-5-nitro-3,4-dihydro-2H-1-benzopyran-3-carboxylic acid.

A mixture of 8-methoxy-5-nitro-3,4-dihydro-2H-1-benzopyran-3-carboxylic acid ethyl ester (5.8 g, 21 mmol) in ethanol (150 mL) and 2 M NaOH (15 mL) was heated to reflux for 30 min. The solvent was evaporated in vacuo the residue dissolved in water. Acidification to pH 2 and extraction with ethyl acetate followed by evaporation of the solvent in vacuo gave 4.9 g (94% yield) of the title compound: mp 181–183° C.; EIMS (70 eV) m/z (relative intensity) 253 (55, $M^+$).

Preparation 45
N-[4-(4-Morpholinyl)phenyl]-8-methoxy-5-nitro-3,4-dihydro-2H-1-benzopyran-3-carboxamide.

To a solution of 8-methoxy-5-nitro-3,4-dihydro-2H-1-benzopyran-3-carboxylic acid (2.5 g, 10 mmol) in toluene (40 mL) and N,N-dimethylformamide (1 mL) was added thionyl chloride (3.6 mL, 50 mmol). The reaction mixture was refluxed for 2 h and the solvent was removed in vacuo. The residual acid chloride was added to a solution of 4-(1-morpholino)aniline (1.78 g, 10 mmol; described in: Devlin, J. P. et. al., *J Chem. Soc. Perkin Trans,* 1. 1975 830–841) and triethylamine (2.0 g, 20 mmol) in methylene chloride (30 mL) and stirred at 0° C. for 10 min and for 1 h at room temperature. The solvent was removed in vacuo and the residue was dissolved in ethyl acetate and washed with 2 M NaOH. Evaporation of the solvent in vacuo afforded 1.5 g (36% yield) of the title compound as white crystals: mp 238–240° C.; EIMS (70 eV) m/z (relative intensity) 413 (5, $M^+$).

Preparation 46
N-[4-(4-Morpholinyl)phenyl]-5-amino-8-methoxy-3,4-dihydro-2H-1-benzopyran-3-carboxamide.

To a solution of N-[4-(4-morpholinyl)phenyl]-8-methoxy-5-nitro-3,4-dihydro-2H-1-benzopyran-3-carboxamide (1.2 g, 2.9 mmol) in N,N-dimethylformamide (10 mL) was added a solution of sodium dithionite (2.1 g, 12 mmol) in water (5 mL). The mixture was stirred at 55° C. for 3 h and the solvent was removed in vacuo. The residue was purified by column chromatography on silica gel using ethyl acetate as the eluent affording 273 mg of the title compound (55% yield): EIMS (70 eV) m/z (relative intensity) 383 (100, $M^+$).

Preparation of the 5-HT$_{1B}$ antagonist compounds described herein

EXAMPLE 1

(R)-N-[8-(Piperazin-1-yl)-1,2,3,4-tetrahydro-2-naphthyl]-4-morpholinobenzamide

To an ice-cooled solution of (R)-N-[8-(4-tert-butyloxycarbonylpiperazin-1-yl)-1,2,3,4-tetrahydro-2-naphthyl]-4-morpholinophenylcarboxamide (1.0 g, 2 mmol) in methylene chloride (100 mL) was added trifluoroacetic acid (3 mL). The reaction was stirred at ambient temperature for 7 h. The solvent was evaporated in vacuo and the residue was dissolved in water (20 mL), alkalized with a 2 M aqueous sodium hydroxide solution and extracted, twice, with methylene chloride. The phases were separated, the combined organic phases were dried (Na$_2$SO$_4$), filtered and evaporated in vacuo. Purification on a silica gel column using chloroform/methanol/concentrated ammonium hydroxide (95:5:0.5) as the eluent gave 580 mg (70% yield) of the title compound as white crystals: mp 202–203° C.; $[\alpha]^{21}_D$–56° (c 1.0, chloroform); EIMS (70 eV) m/z (relative intensity) 420 (5, M$^+$).

EXAMPLE 2

R)-N-[8-(4-Ethylpiperazin-1-yl)-1,2,3,4-tetrahydro-2-naphtbyl]-4-morpholinobenzamide To a solution of (R)-N-8-(piperazin-1-yl)-1,2,3,4-tetrahydro-2-naphthyl]-4-morpholinobenzamide (90 mg, 0.21 mmol) in acetone (20 mL) were added potassium carbonate (44 mg, 0.32 mmol) and iodoethane (26 4L, 0.32 mmol) and the reaction was stirred for 48 h at ambient temperature. The reaction mixture was filtered and the solvent evaporated in vacuo. The residue was partitioned between methylene chloride and water, the phases were separated, and the organic phase was dried (Na$_2$SO$_4$), filtered and evaporated in vacuo. Purification on a silica gel column using chloroform/ethanol saturated with NH$_3$ (100:3) as the eluent gave 63 m;, (66% yield) of the title compound as white crystals: mp: 204–206° C.; $[\alpha]^{21}_D$–67° (c 1.0, chloroform); EIMS (70 eV) m/z (relative intensity) 448 (21, M$^+$).

EXAMPLE 3

(R)-N-[5-Methoxy-8-(4-methylpiperazin-1-yl)-1,2,3,4-tetrahydro-2-naphthyl]-4-morpholinobenzamide To a solution of 4-morpholinobenzoic acid (0.92 g, 4.5 mmol; described in: Degutis, J.;Rasteikiene, L.; Degutiene, A. Zh. *Org. Khim.* 1978, 14(10), 2060–2064) in anhydrous N,N-dimethylformamide (75 mL) was added 1,1'-carbonyldiimidazole (0.76 g, 4.8 mmol) and the reaction was heated at 75° C. When the carbon dioxide evolution had ceased (after 45 min), the reaction was cooled to room temperature and a solution of (R)-2-amino-5-methoxy-8-(4-methylpiperazin-1-yl)-1,2,3,4-tetrahydronaphthalene (1.2 g, 4.2 mmol) dissolved in anhydrous N,N-dimethylformamide (20 mL) was added. The reaction was allowed to stir at ambient temperature for 48 h and the solvent was evaporated in vacuo. Purification on a silica gel column using chloroform/methanol/concentrated ammonium hydroxide (180:5:0.5) as the eluent followed by recrystallization from ethyl acetate and a few drops of methanol gave 1.0 g (53% yield) of white crystals: mp 237–238° C. $[\alpha]^{21}_D$–40 ° (c=1, chloroform); EIMS (70 eV) m/z (relative intensity) 464 (5, M$^+$).

EXAMPLE 4

(R)-N-[5-Ethyl-8-(4-methylpiperazin-1-yl)-1,2,3,4-tetrahydro-2-naphthyl]-4-morpholinobenzamide 4-Morpholinobenzoic acid (64 mg, 0.31 mmol) was dissolved in dry N,N-dimethylformamide (1 mL) and 1,1'-carbonyldiimidazole (52 mg, 0.32 mmol) was added. The reaction mixture was stirred at 75° C. for 1 h and cooled to room temperature. A solution of (R)-2-amino-5-ethyl-8-(4-metylpiperazin-1-yl)-1,2,3,4-tetrahydronaphthalene (80 mg, 0.29 mmol) in dry N,N-dimethylformamide (3 mL) was added and the reaction mixture was stirred at room temperature for 14 h. The solvent was evaporated and the residue was dried in vacuo. The crude product was purified by preparative TLC on silica using chloroform/methanol/conc. NH$_3$ (95:5:0.5) as the eluent which gave 85 mg (59% yield) of the title compound as a white solid: mp 234° C. (dec); EIMS (70 eV) m/z (relative intensity) 462 (27, M$^+$); $[\alpha]^{21}_D$–48° (c 0.09, chloroform).

EXAMPLE 5

(R)-N-[5-Ethyl-8-(4-methylpiperazin-1-yl)-1,2,3,4-tetrahydro-2-naphthyl]-(4-morpholinocarbonyl)benzamide 4-Morpholinocarbonylbenzoic acid (180 mg, 0.77 mmol; described in: *J. Med. Chem.* 1994, 37(26), 4538–4554) and 1,1'-carbonyldiimidazole (130 mg, 0.80 mmol) were dissolved in dry N,N-dimethylformamide (3 mL) and stirred at 75° C. for 2 h. After cooling to room temperature, a solution of (R)-2-amino-5-ethyl-8-(4-methylpiperazin-1-yl)-1,2,3,4-tetrahydronaphthalene (200 mg, 0.73 mmol) in dry N,N-dimethylformamide was added and the reaction mixture was stirred for 60 h. The solvent was evaporated in vacuo and the residue was partitioned between methylene chloride (60 mL) and 2 M NH$_3$ (5 mL). The organic phase was washed with brine (10 mL) and dried (Na$_2$SO$_4$). Evaporation of the solvent in vacuo gave 360 mg of a crude product. Purification by column chromatography on silica using chloroform/methanol/conc. NH$_3$ (95:5:0.5) as the eluent afforded 240 mg (65% yield) of the title compound as a white solid: mp 213–214° C.; EIMS (70 eV) m/z (relative intensity) 490 (27, M$^+$); $[\alpha]^{21}_D$–28° (c 0.15, chloroform).

EXAMPLE 6

(R)-N-[5-Methoxy-8-(4-methylpiperazin-1-yl)-1,2,3,4-tetrahydro-2-naphthyl]-4-morpholinocarbonylbenzamide The title compound was prepared from (R)-2-amino-5-methoxy-8-(4-methylpiperazin-1-yl)-1,2,3,4-tetrahydronaphthalene following the general method of Preparation 16. Purification on a silica gel column using chloroform/methanol/concentrated ammonium hydroxide (96:4:0.3) as the eluent gave after recrystallization from ethyl acetate/diethyl ether 93 mg (52% yield) of white crystals: mp 209–210° C.; $[\alpha]^{21}_D$–18°(c=1, chloroform); EIMS (70 eV) m/z (relative intensity) 492 (36, M$^+$).

EXAMPLE 7

(R)-N-[5-Bromo-8-(piperazin-1-yl)-1,2,3,4-tetrahydro-2-naphthyl]-4-morpholinobenzamide To an ice-cooled solution of (R)-N-[5-bromo-8-(4-tert-butyl oxycarbonylpiperazin-1-yl)-1,2,3,4-tetrahydro-2-naphthyl]-4-morpholinobenzamide (150 mg, 0.26 mmol) in methylene chloride (20 mL) was added trifluoroacetic acid (0.7 mL). The reaction was stirred at ambient temperature for 20 h. The solvent was evaporated in vacuo and the residue was dissolved in water (20 mL), alkalized with a 2 M aqueous solution of sodium hydroxide and extracted with methylene chloride. The phases were separated and the organic phase was dried (Na$_2$SO$_4$), filtered and evaporated in vacuo. The residue was purified on a silica gel column using chloroform /methanol/concentrated ammonium hydroxide (90:10:1) as the eluent. Yield: 94 mg, (72%) of a white crystals: mp 228–229° C.; $[\alpha]^{21}_D$–6° (c=1, chloroform); EIMS (70 eV) m/z (relative intensity) 498 and 500 (1.5, M+)

EXAMPLE 8
(R)-N-[5-Bromo-8-(4-methylpiperazin-1-yl)-1,2,3,4-tetrahydro-2-naphthyl]-4-morpholinobenzamide The title compound was prepared from (R)-2-amino-5-bromo-8-(4-methylpiperazin-1-yl)-1,2,3,4-tetrahydronaphthalene following the general method of Preparation 16. Purification on a silica gel column using chloroform/methanol/concentrated ammonium hydroxide (95:5: 1) as the eluent gave 100 mg (62% yield) of white crystals: mp 245–246° C. $[\alpha]^{21}_D$–23 ° (c=1, chloroform); EIMS (70 eV) m/z (relative intensity) 512 and 514 (1, M+).

EXAMPLE 9
(R)-N-[5-Bromo-8-(4-methylpiperazin-1-yl)-1,2,3,4-tetrahydro-2-naphthyl]-4-trifluoromethylbenzamide (R)-N-[8-(4-methylpiperazin-1-yl)-1,2,3,4-tetrahydro-2-naphthyl]-4-trifluoromethylbenzamide (80 mg, 0.19 mmol) and sodium acetate (200 mg) were dissolved in acetic acid (3 mL) and the mixture was stirred at room temperature. Bromine (34 mg, 0.21 mmol) was added dropwise to the reaction mixture and the mixture was stirred for 2 h at ambient temperature. A 2 M sodium hydroxide solution (100 mL) was added and the mixture was extracted with diethyl ether (2×50 mL). The combined organic phases were dried over anhydrous sodium sulfate, filtered and concentrated in vacuo. Purification on a silica gel column using methylene chloride/ethanol saturated with $NH_3$ (94:6) as the eluent gave 80 mg (85% yield) of the title compound as a white solid: mp 229–230° C.; $[\alpha]^{21}_D$–5.4° (c=1, chloroform); EIMS (70 eV) m/z (relative intensity) 495 and 497 (3, M+).

EXAMPLE 10
(R)-N-[5-Methyl-8-(4-methylpiperazin-1-yl)-1,2,3,4-tetrahydro-2-naphthyl]-4-morpholinobenzamide 4-Morpholinobenzoic acid (92 mg, 0.44 mmol) was dissolved in dry N,N-dimethylformamide (2 mL) and flushed with nitrogen. To the solution was added 1,1'-carbonyldiimidazole (76 mg, 0.47 mmol) and the reaction mixture was stirred at 75° C. for 1.5 h. The solution was cooled to room temperature and (R)-2-amino-5-methyl-8-(4-methylpiperazin-1-yl)-1,2,3,4-tetrahydronaphthalene (110 mg, 0.42 mmol), dissolved in dry N,N-dimethylformamide (2 mL) was added. The solution was stirred at room temperature for 30 h. The solvent was evaporated in vacuo giving 290 mg of a crude product. Purification by preparative TLC on silica gel using chloroform/methanol/conc. $NH_3$ (95:5:0.5) as the eluent afforded 145 mg (73% yield) of the title compound as a white solid: mp>231° C. (dec); EIMS (70 eV) m/z (relative intensity) 448 (3, M+); $[\alpha]^{21}_D$–60° (c 0.15, chloroform).

EXAMPLE 11
N-(4-Morpholinophenyl)-8-(4-methylpiperazinyl)-5-methoxy-1,2,3,4-tetrahydronaphthalene-2-carboxamide A solution of N-(4-morpholinophenyl)-8-amino-5-methoxy-1,2,3,4-tetrahydronaphthalene-2-carboxamide (1.4 g, 3.5 mmol), bis (2-chloroethyl)-methylamine hydrochloride (960 mg, 5 mmol) and sodium hydrogen carbonate (420 mg, 5 mmol) in n-butanol (30 mL) was heated at 90° C. for 5 h. After cooling, 2 M ammonium hydroxide (30 mL) was added and the mixture heated at 50° C. for 1 h. The phases were separated, evaporated in vacuo and purified by flash chromatography on a silica gel column with chloroform/ethanol/conc. ammonium hydroxide 90/10/0.3 as eluent. Yield: 320 mg (20%) of the title compound: mp 230–232° C.; EIMS (70 eV) m/z (relative intensity) 464 (75, M+).

Chromatographic Preparation of the Enantiomers of N-(4-Morpholinophenyl)-8-(4-methylpiperazinyl)-5-methoxy-1,2,3,4-tetrahydronaphthalene-2-carboxamide N-(4-Morpholinophenyl)-8-(4-methylpiperazinyl)-5-methoxy-1,2,3,4-tetrahydronaphthalene-2-carboxamide (5 mg) was dissolved in 4 ml of eluent consisting of acetonitrile and pH 3.0 phosphate buffer, $\mu$=0.1 (62.5 : 37.5, v/v). This solution was purified on a Nucleosil 7 $C_{18}$ column (25×250 mm) with the above mobile phase to remove late eluting impurities. The collected fractions of the main component were concentrated under reduced pressure at 35–39° C. The residue was dissolved in 30 ml of the eluent composed of 10 mM ammonium acetate, diethylamine and acetic acid (4000+2+2, v/v/v, pH 5.26) and the chiral semi-preparation of the enantiomers of N-(4-morpholinophenyl)-8-(4-methylpiperazinyl)-5-methoxy-1,2,3,4-tetrahydronaphthalene-2-carboxamide was carried out on a Chiral AGP semi-prepative column (10×150 mm) using a guard column of the same stationary phase. 2.0 ml/min of flow rate was used and detection was monitored at 260 nm. Fractions of both enantiomers were separately collected and concentrated to a volume of about 5 ml under reduced pressure at 35–39° C. The concentrated fractions were adjusted to pH 10–11 with 5 M NaOH and extracted with chloroform. The two organic phases were washed with water and dried with anhydrous magnesium sulfate. After being filtered through glasswool, the organic filtrates were evaporated in vacuo affording the two enantiomers as two slightly yellow solids.

EXAMPLE 12
N-(Morpholinocarbonylphenyl)-8-(4-methylpiperazin-1-yl)-5-methoxy-1,2,3,4-tetrahydronaphthalene-2-carboxamide A solution of N-(morpholinocarbonylphenyl)-8-amino-5-methoxy-1,2,3,4-tetrahydronaphthalene-2-carboxamide (280 mg, 0.69 mmol), bis (2-chloroethyl)methyl amine hydrochloride (190 mg, 1.0 mmol) and sodium hydrogen carbonate (84 mg, 1.0 mmol) in n-butanol (20 mL) was heated at 90° C. for 5 h. After cooling, 2 M ammonium hydroxide (10 mL) was added and the mixture was heated at 50° C. for 1 h. The organic phase was evaporated in vacuo and the residue was purified by flash chromatography on a silica gel column using chloroform/ethanol/conc. ammonium hydroxide (90:10:0.5) as eluent to yield 60 mg (18%) of the title compound: EIMS (70 eV) m/z (relative intensity) 492 (50, M+).

EXAMPLE 13
(S)-N-[5-(4-Methylpiperazin-1-yl)-3,4-dihydro-2H-1-benzopyran-3-yl]-4-morpholinobenzamide.

A solution of 4-morpholinobenzoic acid (380 mg, 1.83 mmol, described in: Degutis, J.; Rasteikiene, L.; Degutiene, A. Zh. *Org. Khim.* 1978, 14(10), 2060–2064) and 1,1'-carbonyldiimidazole (310 mg, 1.92 mmol) in anhydrous N,N-dimethylformamide (12 mL) was stirred at 75° C. for 30 min. The mixture was allowed to cool after which a solution of (S)-3-amino-5-(4-methylpiperazin-1-yl)-3,4-dihydro-2H-1-benzopyran (430 mg, 1.74 mmol) in N,N-dimethylformamide (8 mL) was added. The reaction mixture was stirred at room temperature for 3 days. Another portion of 1,1'-carbonyldiimidazole (57 mg, 0.35 mmol) was added, and the mixture was stirred for an additional 3.5 h. The solvent was removed in vacuo, and the residue was purified by column chromatography on silica (eluent: chloroform/ ethanol; 93:7+0.5% NH$_3$) affording 513 mg (68% yield) of the title compound as a white solid: mp 210–212° C.; $[\alpha]^{22}_D$–145° (c 1.0, chloroform); EIMS (70 eV) m/z (relative intensity) 436 (65, M$^+$).

EXAMPLE 14
(S)-N-[5-(4-Methylpiperazin-1-yl)-3,4-dihydro-2H-1-benzopyran-3-yl]-4-(4-piperidon-1-yl)benzamide.

A solution of 1,1'-carbonyldiimidazole (116 mg, 0.716 mmol) and 4-(4-piperidon-1-yl)benzoic acid (150 mg, 0.683 mmol) in anhydrous N,N-dimethylformamide (5 mL) was stirred at 75° C. for 50 min. The mixture was allowed to cool, and a solution of (S)-3-amino-5-(4-methylpiperazin-1-yl)-3,4-dihydro-2H-1-benzopyran (161 mg, 0.651 mmol) in N,N-dimethylformamide (4 mL) was added. The reaction mixture was stirred at room temperature for 8 days. The solvent was removed in vacuo, and the residue was purified by column chromatography on silica (eluent: chloroform/ ethanol, 90:10+0.5% conc. NH$_3$) affording 54 mg (19% yield) of the title compound as a white solid: mp 222–225° C. (decomposes); $[\alpha]^{22}_D$–136° (c 0.30, chloroform); TSPMS (70 eV) m/z 449 (M+1).

EXAMPLE 15
(S)-N-[8-Methyl-5-(4-methyl-piperazin-1-yl)-3,4-dihydro-2H-1-benzopyran-3-yl]-4-(dimethylaminocarbonyl)benzamide 4-(Dimethylaminocarbonyl)benzoic acid (Jurewicz, A. T; U.S. Pat. No. 3,607,918 1971) (38 mg, 0.20 mmol) and 1,1'-carbonyldiimidazole (34 mg, 0.21 mmol) were dissolved in dry N,N-dimethylformamide (4 mL) and stirred at 75° C. for 1.5 h. The reaction mixture was cooled to room temperature and a solution of (S)-3-amino-8-methyl-5-(4-methylpiperazin-1-yl)-3,4-dihydro-2H-1-benzopyran (49 mg, 0.19 mmol) in dry N,N-dimethylformamide (5 mL) was addded. The reaction mixture was stirred at 50° C. for 14 h and the solvent was evaporated in vacuo giving 120 mg of a crude product. Purification by preparative TLC using chloroform/ methanol/conc.NH$_3$ (95:5:0.5) as the eluent afforded 40 mg (48% yield) of the title compound as a white foam: EIMS (70 eV) m/z (relative intensity) 436 (26, M$^+$); $[\alpha]^{21}_D$–9° (c 0.20, chloroform).

EXAMPLE 16
N-[4-(4-Morpholinyl)phenyl]-8-methoxy-5-(4-methyl-piperazin-1-yl)-3,4-dihydro-2H-1-benzopyran-3-carboxamide.

A solution of N-[4-(4-morpholinyl)phenyl]-5-amino-8-methoxy-3,4-dihydro-2H-1-benzopyran-3-carboxamide (270 mg, 0.7 mmol), bis (2-chloroethyl)-methylamine hydrochloride (288 mg, 1.5 mmol) and sodium hydrogen carbonate (126 mg, 1.5 mmol) in n-butanol (10 mL) was stirred at 90° C. for 2.5 h. 2 M ammonia (10 mL) was added at 50 ° C., the mixture was cooled and the phases were separated. The organic phase evaporated in vacuo and the residue was purified by column chromatography on silica gel using ethyl acetate/triethyl amine (100:8) as the eluent affording 170 mg (50% yield) of the title compound as white crystals: mp 202–204° C.; EIMS (70 eV) m/z (relative intensity) 466 (100 M$^+$).

EXAMPLE 17
(R)-N-[8-(4-Methylpiperazin-1-yl)-1,2,3,4-tetrahydro-2-naphthyl]-4-morpholinobenzamide To a solution of 4-morpholinobenzoic acid (0.89 g, 4.3 mmol; described in: Degutis, J.; Rasteikiene, L.; Degutiene, A. Zh. *Org. Khim.* 1978, 14(10), 2060–2064) in anhydrous N,N-dimethylformamide (30 mL) was added 1,1'-carbonyldiimidazole (0.73 g, 4.3 mmol) and the reaction was heated at 75° C. When the carbon dioxide evolution had ceased (after 30 min), the reaction was cooled to room temperature and a solution of (R)-2-amino-8-(4-methylpiperazin-1-yl)-1,2,3,4-tetrahydronaphthalene (1.0 g, 4.1 mmol) in anhydrous N,N-dimethylformamide (5 mL) was added. The reaction was allowed to stir at ambient temperature for 24 h and the solvent was evaporated in vacuo. Purification on a silica gel column using chloroform/ methanol/ concentrated ammonium hydroxide (95:5:0.5) as the eluent gave 1.5 g (85% yield) of the title compound as white crystals: mp 230–231° C.; $[\alpha]^{21}_D$–49° (c 1.0, chloroform); EIMS (70 eV) m/z (relative intensity) 434 (10, M$^+$).

Pharmacology
Methods for testing
(i) Functional h5-HT$_{1B}$ receptor assay

In order to evaluate the antagonistic properties of the 5-HT$_{1B}$-receptor the standard assay using electrical field stimulation of [$^3$H]-5-HT release from occipital cortex of guinea pigs can be used.

Methods and Materials:

Buffer composition (mM) NaHCO$_3$ (25), NaH$_2$PO$_4$. H$_2$O (1.2), NaCl (117), KCl(6), MgSO$_4$x7H$_2$O(1.2), CaCl$_2$(1.3), EDTA Na$_2$(0.03). The buffer is gassed for at least 30 min before use. The pH of the buffer is about 7.2 of room temperature but it rises to about 7.4 at 37° C.

Preparation of occipital cortical slices

Guinea pigs (200–250 g) were decapitated and the whole brains were removed. The occipital cortieces were dissected and cut into slices 0.4×4 mm with a McIlwain chopper machine. The white part of the tissue was removed carefully with a tweezer before slicing. The slices were incubated in 5 ml buffer in the presence of 5 mM pargyline chloride. After incubation with 0.1 mM [$^3$H]-5-HT for another 30 min the slices were transferred to a test tube and washed three times with the same volume of buffer. The slices were transferred to the superfusion chambers with a plastic pipette and were washed for 40 min. with the buffer in the presence of uptake inhibitor citalopram (2.5 μM) with a flow of 0.5 ml/min.

Electrical stimulation of 5-HT release

The superfused buffer was collected in 2 ml fractions. The slices were stimulated by electricity with a train of pulses of frequency 3 Hz, duration 2 ms and current 30 mA for 3 min at the 4th and 13th fractions. The tested drugs were added from the 8th fraction to the end of the experiment.

Results

A first electrical (or K$^+$) stimulation resulted in a standard amount of [$^3$H] 5-HT released (S$_1$). Between the first and second stimulation the h5-HT$_{1B}$ antagonist is added to the media which results in a dose depending increase of the release(S$_2$) during the second stimulation. The S$_2$/S$_1$ ratio which is the per cent of released [$^3$H] 5-HT at the second stimulation (S$_2$) divided by that of the first stimulation (S$_1$) was used to estimate drug effects on transmitter release. See FIG. 1.

(ii) The effect of a h5-HT$_{1B}$ receptor antagonist in combination with a monoamine oxidase inhibitor on extracellular levels of 5-HT in the guinea pig frontal cortex as measured by in vivo microdialysis.

Male Dunkin Hartley guinea pigs (Mollegaard and Harlan, Germany), weighing 350–500 g, were anaesthetized intramuscularly with a 1:3 v/v mixture of Rompun® vet (20 mg/ml) and Ketalar® vet (50 mg/ml) and placed in a stereotaxic frame. A unilateral guide cannula was carefully implanted into the frontal cortex using the following stereotaxic koordinates with respect to bregma: AP: +4.5 mm, L: −2.0 mm and DV: 0 mm from the brain surface. The animals were then allowed to recover for 2–7 days before the experiments were carried out. The day before starting dialysis sampling, microdialysis probes with 3 mm membranes were inserted into the guide cannula. The probes were perfused with Ringer solution at a flow rate of 2.0 μl/min and samples were collected every 20 min. Compound A (monoamine oxidase inhibitor, MAOI) was given at time 0 min and compound B or C (h5-$HT_{1B}$ antagonist or saline) was administered 60 min later. All drugs were given subcutaneously. The 5-HT content was analyzed by high performance liquid chromatography (HPLC) with electrochemical detection. For data analysis, the average 5-HT value of 3–4 samples collected pre-administration of drugs was defined as 100% (baseline) and the following samples expressed as percent of this value.

FIG. 2 shows the effects of compound A in combination with compound B or C on extracellular levels of 5-HT in the guinea pig frontal cortex. Data are mean ±S.E.M; n=5. The arrows indicate drug administration.

Compound A: Pheneizine
Compound B: Saline
Compound C: (R)-N-[5-Methyl-8-(4-methylpiperazin-1-yl)-1,2,3,4-tetrahydro-2-naphthyl]-4-morpholinobenzamide

What is claimed is:

1. A combination comprising a first component (a) which is a monoamine oxidase inhibitor and a second component (b) which is a selective h5-$HT_{1B}$ antagonist or partial agonist having the formula I

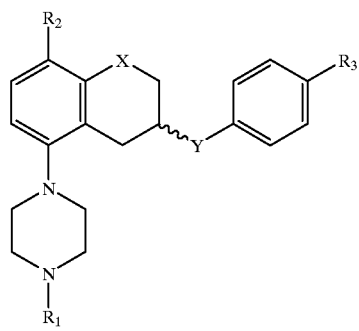

(I)

wherein X is $CH_2$, or O;
Y is CONH, or NHCO;
$R_1$ is H, $C_1$–$C_6$ alkyl, or $C_3$–$C_6$ cycloalkyl;
$R_2$ is H, $C_1$–$C_6$ alkyl, $C_1$–$C_6$ alkoxy, or halogen;
$R_3$ is

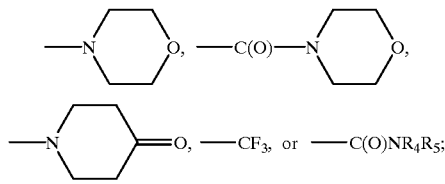

$R_4$ and $R_5$ independently are H or $C_1$–$C_4$ alkyl, wherein the component (b) is in the racemate, R-enantiomer or S-enantiomer form, and wherein said components (a) and (b) are in the form of a free base, solvate or pharmaceutically acceptable salt thereof.

2. The combination according to claim 1 wherein the second component (b) is a compound of formula I wherein X is $CH_2$.

3. The combination according to claim 2 wherein the second component (b) is a compound of formula I wherein Y is NHCO.

4. The combination according to claim 3 wherein the second component (b) is a compound of formula I wherein $R_3$ is morpholino.

5. The combination according to claim 1 wherein the second component (b) is a compound of formula I wherein $R_1$ is hydrogen, methyl or ethyl and $R_2$ is hydrogen, methyl, ethyl, methoxy or bromo.

6. The combination according to claim 1 wherein the second component (b) is a compound selected from the group consisting of
(R)-N-[8-(Piperazin-1-yl)-1,2,3,4-tetrahydro-2-naphthyl]-4-morpholinobenzamide;
(R)-N-[8-(4-Ethylpiperazin-1-yl)-1,2,3,4-tetrahydro-2-naphthyl]-4-morpholinobenzamide;
(R)-N-[8-(4-Methylpiperazin-1-yl)-1,2,3,4-tetrahydro-2-naphthyl]-4-morpholinobenzamide;
(R)-N-[5-Methoxy-8-(4-methylpiperazin-1-yl)-1,2,3,4-tetrahydro-2-naphthyl]-4-morpholinobenzamide;
(R)-N-[5-Ethyl-8-(4-methylpiperazin-1-yl)-1,2,3,4-tetrahydro-2-naphthyl]-4-morpholinobenzamide;
(R)-N-[5-Ethyl-8-(4-methylpiperazin-1-yl)-1,2,3,4-tetrahydro-2-naphthyl]-4-morpholinocarbonyl benzamide;
(R)-N-[5-Methoxy-8-(4-methylpiperazin-1-yl)-1,2,3,4-tetrahydro-2-naphthyl]-4-morpholinocarbonylbenzamide;
(R)-N-[5-Bromo-8-(piperazin-1-yl)-1,2,3,4-tetrahydro-2-naphthyl]-4-morpholinobenzamide;
N-[5-Bromo-8-(4-methylpiperazin-1-yl)-1,2,3,4-tetrahydro-2-naphthyl]-4-morpholinobenzamide;
(R)-N-[5-Bromo-8-(4-methylpiperazin-1-yl)-1,2,3,4-tetrahydro-2-naphthyl]-4-trifluoromethylbenzamide;
(R)-N-[5-Methyl-8-(4-methylpiperazin-1-yl)-1,2,3,4-tetrahydro-2-naphthyl]-4-morpholinobenzamide;
N-(4-Morpholinophenyl)-8-(4-methylpiperazinyl)-5-methoxy-1,2,3,4-tetrahydronaphthalene-2-carboxamide;
(R)-N-(4-Morpholinophenyl)-8-(4-methylpiperazinyl)-5-methoxy-1,2,3,4-tetrahydronaphthalene-2-carboxamide;
(S)-N-(4-Morpholinophenyl)-8-(4-methylpiperazinyl)-5-methoxy-1,2,3,4-tetrahydronaphthalene-2-carboxamide;
(R)-N-(Morpholinocarbonylphenyl)-8-(4-methylpiperazin-1-yl)-5-methoxy-1,2,3,4-tetrahydronaphthalene-2-carboxamide;
(S)-N-[5-(4-Methylpiperazin-1-yl)-3,4-dihydro-2H-1-benzopyran-3-yl]-4-morpholinobenzamide;
(S)-N-[5-(4-Methylpiperazin-1-yl)-3,4-dihydro-2H-1-benzopyran-3-yl]-4-($^4$-piperidon-1-yl)benzamide;
(S)-N-[8-Methyl-5-(4-methyl-piperazin-1-yl)-3,4-dihydro-2H-1-benzopyran-3-yl]-4-(dimethylaminocarbonyl)benzamide; and
N-[4-(4-Morpholinyl)phenyl]-8-methoxy-5-(4-methyl-piperazin-1-yl)-3,4-dihydro-2H-1-benzopyran-3-carboxamide, wherein said compounds are in the form of free base, solvate or pharmaceutically acceptable salt thereof.

7. The combination according to claim 6 wherein the second component (b) is a compound selected from the group consisting of (R)-N-[$^8$-(4-Methylpiperazin-1-yl)-1,2, 3,4-tetrahydro-2-naphthyl]-4-morpholinobenzamide, (R)-N-[5-Methoxy-8-(4-methylpiperazin-1-yl)-1,2,3,4-tetrahydro-2-naphthyl]-4-morpholinobenzamide and (R)-N-[5-Methyl-8-(-4-methylpiperazin-1-yl)-1,2,3,4-tetrahydro-2-naphthyl]-4-morpholinobenzamide.

8. The combination according to any one of claims 1–7 wherein the monoamine oxidase inhibitor is moclobemide or phenelzine.

9. A method for the treatment of affective disorders by administering to a patient suffering therefrom a therapeutically effective amount of the combination of claim 1.

10. A method for the treatment of depression by administering to a patient suffering therefrom a therapeutically effective amount of the combination of claim 1.

11. A pharmaceutical formulation comprising the combination defined in claim 1 as active ingredients.

12. The pharmaceutical formulation according to claim 11 wherein the first component (a) is concomitantly administered with the second component (b).

13. A process for the preparation of the combination according to claim I comprising incorporating the first component (a), which is a monoamine oxidase inhibitor and the second component (b), which is a selective 5-HT$_{1B}$ antagonist or partial agonist into one pharmaceutical formulation.

14. A process for the preparation of the combination according to claim 1 comprising the preparation of the component (a), which is a monoamine oxidase inhibitor, and the component (b), which is a selective 5-HT$_{1B}$ antagonist or partial agonist, and combining components (a) and (b) into the same pharmaceutical formulation.

15. A kit containing the combination according to claim 1, optionally with instructions for use.

16. A method of improving the onset of therapeutic action comprising the concomitant administration of a therapeutically effective amount of the combination according to claim 1.

17. The pharmaceutical formulation according to claim 11, further comprising adjuvants, diluents, excipients or inert carriers.

18. The pharmaceutical formulation according to claim 12, wherein the first component (a) is concomitantly administered with the second component (b) in a single dosage form.

19. The pharmaceutical formulation according to claim 12, wherein the first component (a) is concomitantly administered with the second component (b) in separate dosage forms for each component.

20. A method for the treatment of affective disorders by administering to a patient suffering therefrom a therapeutically effective amount of the pharmaceutical formulation of claim 11.

21. A method for the treatment of depression by administering to a patient suffering therefrom a therapeutically effective amount of the pharmaceutical formulation of claim 11.

22. The method according to any one of claim 9, 10, 16, 20 and 21, wherein the first component (a) is concomitantly administered with the second component (b) in a single dosage form.

23. The method according to any one of claims 9, 10, 16, 20 and 21, wherein the first component (a) is concomitantly administered with the second component (b) in separate dosage forms for each component.

* * * * *

UNITED STATES PATENT AND TRADEMARK OFFICE
CERTIFICATE OF CORRECTION

PATENT NO.   : 6,159,970
DATED        : December 12, 2000
INVENTOR(S)  : Berg et al.

It is certified that error appears in the above-identified patent and that said Letters Patent is hereby corrected as shown below:

Title page,
"H5-HT$_{1B}$" should read -- h5-HT$_{1B}$ --.
Assignee name "Astrazeneca AB" should read -- AstraZeneca AB --.

Claim 6, column 42,
Line 56, "($^4$-piperidon-1-yl) benzamide" should read -- (4-piperidon-1-yl) benzamide --.

Claim 7, column 42,
Line 67, "$^8$-(4-Methylpiperazin-1-yl)" should read -- 8-(4-Methylpiperazin-1-yl) --.

Signed and Sealed this

Twenty-fifth Day of September, 2001

*Attest:*

*Nicholas P. Godici*

*Attesting Officer*

NICHOLAS P. GODICI
*Acting Director of the United States Patent and Trademark Office*